(12) United States Patent
Udale et al.

(10) Patent No.: US 12,708,482 B2
(45) Date of Patent: Aug. 18, 2026

(54) IMPLANTABLE FERROMAGNETIC MARKERS

(71) Applicant: ENDOMAGNETICS LTD., Cambridge (GB)

(72) Inventors: Robinson Udale, Cambridgeshire (GB); Gabriel Villar, Cambridgeshire (GB)

(73) Assignee: ENDOMAGNETICS LTD. (GB)

( * ) Notice: Subject to any disclaimer, the term of this patent is extended or adjusted under 35 U.S.C. 154(b) by 0 days.

(21) Appl. No.: 18/707,092

(22) PCT Filed: Nov. 3, 2022

(86) PCT No.: PCT/GB2022/052775
§ 371 (c)(1),
(2) Date: May 2, 2024

(87) PCT Pub. No.: WO2023/079288
PCT Pub. Date: May 11, 2023

(65) Prior Publication Data
US 2025/0025260 A1 Jan. 23, 2025

(30) Foreign Application Priority Data
Nov. 3, 2021 (GB) ..................................... 2115826
Nov. 3, 2021 (GB) ..................................... 2115827

(51) Int. Cl.
*A61B 90/00* (2016.01)
*A61B 5/06* (2006.01)
*G01R 33/16* (2006.01)

(52) U.S. Cl.
CPC .............. *A61B 90/39* (2016.02); *A61B 5/062* (2013.01); *A61B 2090/3958* (2016.02); *A61B 2090/3983* (2016.02); *G01R 33/16* (2013.01)

(58) Field of Classification Search
CPC .. A61B 90/39; A61B 2090/3904–3995; A61B 5/062; G01R 33/02
See application file for complete search history.

(56) References Cited

U.S. PATENT DOCUMENTS 5,650,236 A 7/1997 Hirano et al.
5,664,582 A 9/1997 Szymaitis
(Continued)

FOREIGN PATENT DOCUMENTS

CN 101711700 5/2010
CN 111885978 11/2020
(Continued)

OTHER PUBLICATIONS

Chouhan et al. 25—Magnetism of zirconium dioxide (ZrO2), Woodhead Publishing Series in Electronic and Optical Materials, 2023, p. 585-602. Doi: 10.1016/B978-0-323-90907-5.00022-1. (Year: 2023).*
(Continued)

*Primary Examiner* — Anh Tuan T Nguyen
*Assistant Examiner* — Younhee Choi
(74) *Attorney, Agent, or Firm* — K&L GATES LLP

(57) ABSTRACT

There is provided an implantable marker for use in surgical guidance. The implantable marker comprises one or more ferromagnetic elements formed of at least one ferromagnetic material and at least one diamagnetic element formed of at least one diamagnetic material. The at least one diamagnetic material comprises graphite having a substantially isotropic grain structure and the one or more ferromagnetic elements are juxtaposed the at least one diamagnetic element.

20 Claims, 15 Drawing Sheets

(56) References Cited

U.S. PATENT DOCUMENTS

| | | | |
|---|---|---|---|
| 5,921,583 A | 7/1999 | Matsumoto et al. | |
| 6,140,727 A | 10/2000 | Goto et al. | |
| 6,173,715 B1 | 1/2001 | Sinanan et al. | |
| 6,230,038 B1 | 5/2001 | von Gutfeld et al. | |
| 7,135,978 B2 * | 11/2006 | Gisselberg | A61B 5/6883 340/572.8 |
| 7,658,903 B2 | 2/2010 | Miller et al. | |
| 8,676,295 B2 | 3/2014 | Cunningham et al. | |
| 2003/0085703 A1 | 5/2003 | Gleich | |
| 2004/0127787 A1 | 7/2004 | Dimmer et al. | |
| 2005/0033157 A1 * | 2/2005 | Klein | A61B 90/39 600/411 |
| 2005/0059879 A1 | 3/2005 | Sutherland et al. | |
| 2006/0293581 A1 | 12/2006 | Plewes et al. | |
| 2008/0063590 A1 * | 3/2008 | Miller | C04B 35/532 264/29.7 |
| 2010/0076556 A1 | 3/2010 | Tomantschger et al. | |
| 2011/0166439 A1 | 7/2011 | Pfeffer et al. | |
| 2015/0011861 A1 | 1/2015 | Rahmer et al. | |
| 2015/0264891 A1 | 9/2015 | Brander et al. | |
| 2017/0252124 A1 | 9/2017 | Greene et al. | |
| 2017/0263358 A1 * | 9/2017 | Navarro Perez | H01Q 7/06 |
| 2017/0368209 A1 | 12/2017 | Alqathami | |
| 2018/0142423 A1 | 5/2018 | Manov et al. | |
| 2019/0223975 A1 | 7/2019 | Agostinelli et al. | |
| 2021/0153970 A1 | 5/2021 | Agostinelli et al. | |

FOREIGN PATENT DOCUMENTS

| | | |
|---|---|---|
| DE | 103 54 361 | 6/2005 |
| EP | 2305114 A1 | 4/2011 |
| EP | 3 517 068 | 7/2019 |
| GB | 2582123 | 1/2018 |
| JP | HO6-249934 A | 9/1994 |
| JP | 2010-227244 | 10/2010 |
| JP | 2011-520538 | 7/2011 |
| JP | 2013-514847 | 5/2013 |
| JP | 2015-515288 | 5/2015 |
| JP | 2020078628 A | 5/2020 |
| WO | 2004/091408 | 10/2004 |
| WO | 2006/102235 | 9/2006 |
| WO | 2006/119645 A1 | 11/2006 |
| WO | 2011/067576 | 6/2011 |
| WO | 2011/075839 | 6/2011 |
| WO | 2013/114247 | 8/2013 |
| WO | 2014/013235 | 1/2014 |
| WO | 2014/032235 | 6/2014 |
| WO | 2014/140566 | 9/2014 |
| WO | 2014/140567 | 9/2014 |
| WO | 2016/193753 | 12/2016 |
| WO | 2019180580 | 9/2019 |

OTHER PUBLICATIONS

Translation of Japanese Office Action issued for Japanese Patent Application No. 2024-524601; (3 pages).
PCT International Search Report and PCT Written Opinion for PCT International Application No. PCT/GB2022/052775; mailed from the European Patent Office on Feb. 7, 2023; (14 pages).
Modern Problems in Condensed Matter Sciences vol. 20, Issue 1, 1988, p. 175.
Magnetic susceptibility of the elements and inorganic compounds, pp. 4-130 to 4-135.
Screencapture-web-archive-org-web-20211009021553-http-hyperphysics-phy-astr-gsu-edu-hbase-tables-magprop-html-2023-12-15-17_13_59 (2 pages).
Screencapture-web-archive-org-web-20200127081810-https-mwi-inc-com-high-temperature-graphite-2023-12-15-17_20_24 (2 pages).
Lapine et al., "Broadband diamagnetism in anistropic metamaterials", Physical Review B 87, 024408 (2013) (7 pages).
Magnus et al., "A DC magnetic metamaterial", 2008 (7 pages).
Screencapture-web-archive-org-web-20200501160132-https-www-endomag-com-magseed-overview-2023-12-15-17_24_05 (5 pages).
Reig et al., "Role of MRI to Assess Response to Neoadjuvant Therapy for Breast Cancer", 2020 International Society for Magnetic Resonance in Medicine, vol. 52, No. 6, pp. 1587-1606.
Gao et al. "Reduction of artifact of metallic implant in magnetic resonance imaging by combining paramagnetic and diamagnetic materials", Journal of Applied Physics, Jun. 2010 (6 pages).
Chalakuzhiyl et al., "Interactions between magnetic resonance imaging and dental material", Journal of Pharmacy and Bioallied Sciences, Jun. 2013, vol. 5, Supplement 1, (4 pages).
Cobalt, Essential to High Performance Magnetics, The Cobalt Conference—2012, (22 pages).
Screencapture-web-archive-org-web-20210128045136-https-www-graphitestore-com-custom-machining-2024-04-16-11_42_58, (2 pages).
Screencapture-web-archive-org-web-20210508051413-https-www-semcocarbon-com-capabilities-graphite-machining-2024-04-16-11_41_26, (2 pages).
Screencapture-azom-article-aspx-2024-04-16-11_18_31, (3 pages).
Em007693270, (3 pages).
Screencapture-web-archive-org-web-20210429061527-https-www-endomag-com-sentimag-2023-12-15-17_13_05, (5 pages).
Hargreaves et al., "Metal Induced Artifacts in MRI", AJR Am J Roentgenol, Sep. 2011, 197(3), 547-555.
Masood, "Neoadjuvant chemotherapy in breast cancers", Women's Health, 2016, vol. 12(5), pp. 480-491.
Koh et al., "Introduction of a New Staging System of Breast Cancer for Radiologists: An Emphasis on the Prognostic Stage", Korean Journal of Radiology ,2019, 20(1), pp. 69-82.
Combined UK Search & Examination Report dated Mar. 16, 2022 for application No. GB2115827.4, (6 pages).
PCT International Search Report and PCT Written Opinion for PCT International Application No. PCT/GB2022/052775 mailed from the European Patent Office on Feb. 8, 2023, (15 pages).
Varga et al., "Magnetically Bistable Microwires: Properties and Applications for Magnetic Field, Temperature, and Stress Sensing", Chapter 8, (44 pages).
Sulla et al., "Utilizing Magnetic Microwires for Sensing in Biological Applications", Journal of Electrical Engineering, vol. 66. No. 7/s, 2015, pp. 161-163.
Baranov, "Cast Amorphous Magnetic Microwires for Medical Locator Applications", 2nd International Conference on Nanotechnologies and Biomedical Engineering, Chisinau, Republic of Moldova, Apr. 18-20, 2013, pp. 589-592.
Extracts from High performance Soft Magnetic Materials 2017, Springer Series in Material Science, vol. 252, (60 pages).
Thiruchelvam et al., "Abstract P3-01-17: Mri study of a novel paramagnetic seed for clinically occult breast tumor localization", AACR Journals, Poster Session Abstracts, vol. 82, Issue 4 Supplement, Feb. 15, 2022, (2 pages).
Schenck, "The role of magnetic susceptibility in magnetic resonance imaging: MRI magnetic compatibility of the first and second kinds", Med. Phys., 23 (6), Jun. 1996, pp. 815-850.
Zhou et al., "Paramagnetic electrodes and bulk magnetic susceptibility effects in the in situ NMR studies of batteries: Application to Li 1.08Mn1.9204 spinels", Journal of Magnetic Resonance, 234, (2013) pp. 44-57.
Magnetic Susceptibility of Graphite and Carbon Materials, Chapter 9, pp. 175-196.
Sigrafine® extruded and vibration molded graphite, (3 pages).
Canadian Office Action for Application No. 3,236,559; for application No. GB2022052775, dated May 10, 2024, (4 pages).
End-025CN, China First Office Action for Chinese application No. 202280046399X, dated May 7, 2024, (6 pages).
Colombo et al., "Imaging Magnetic Nanoparticle Distributions by Atomic Magnetometry-Based Susceptometry", IEEE Transactions on Medical Imaging, vol. 39, No. 4, Apr. 2020 (12 pages).
Huanfeng Zhu et al., "Nature of charge transport and p-electron ferromagnetism in nitrogen-doped ZrO2: An ab initio perspective", Scientific Reports, 2015, (6 pages).
Canadian Office Action for Canadian Patent Application No. 3,236,559, dated Sep. 17, 2025, (5 pages).
Japanese Office Action (with English translation) for Japanese Patent Application No. 2024-524601, dated Sep. 19, 2025, (5 pages).

(56) References Cited

OTHER PUBLICATIONS

Non-final Office Action issued by the USPTO on Jul. 3, 2025 for U.S. Appl. No. 18/706,356 (7 pages).
Non-final Office Action issued by the USPTO on Jun. 11, 2025 for U.S. Appl. No. 18/575,610 (9 pages).

* cited by examiner

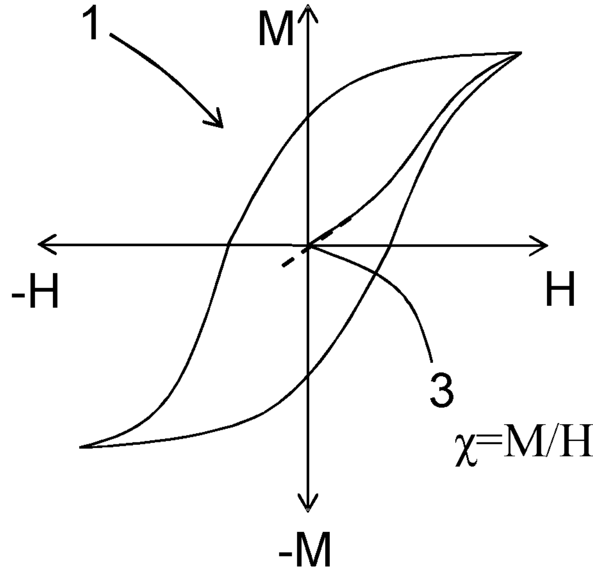
Fig. 2(a)
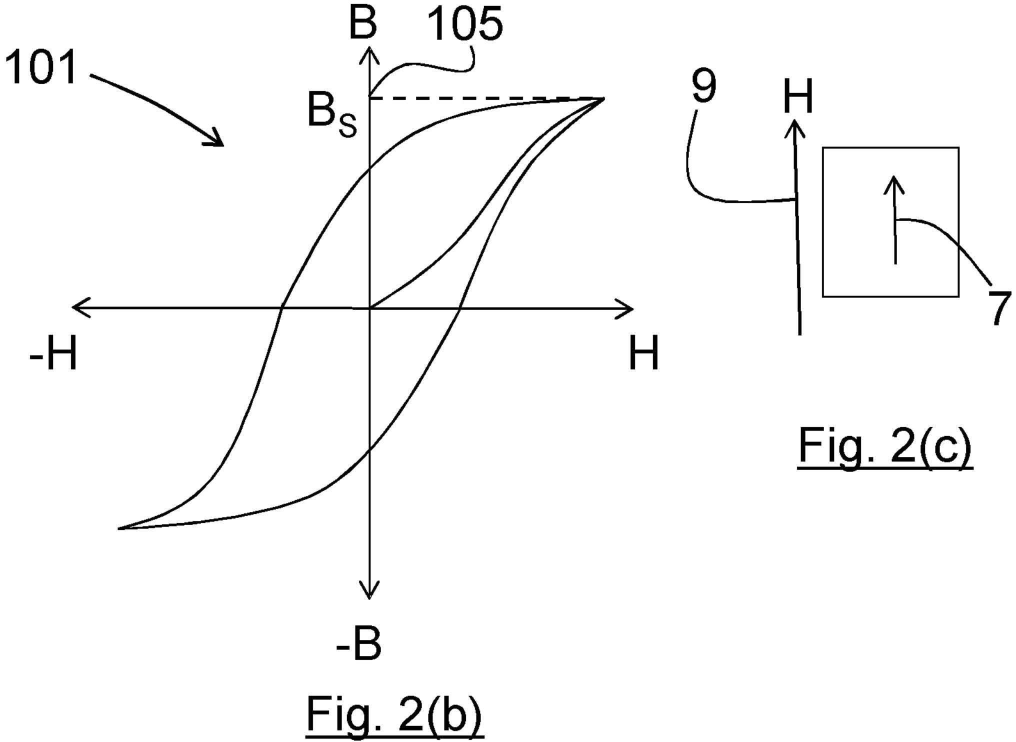
Fig. 2(b)
Fig. 2(c)

0.2 μT
0.4 μT
0.6 μT
0.8 μT
1.0 μT
1113
1111
10 mm
10 mm 0.2 μT
0.4 μT
0.6 μT
0.8 μT
1.0 μT
1107
1109
10 mm
10 mm

IMPLANTABLE FERROMAGNETIC MARKERS

CROSS REFERENCE TO RELATED APPLICATIONS

This is the national phase under 35 U.S.C. § 371 of International Application No. PCT/GB2022/052775 filed on Nov. 3, 2022, which claims priority to and the benefit of United Kingdom Patent Application Nos. 2115827.4 filed on Nov. 3, 2021 and 2115826.6 filed on Nov. 3, 2021, the entire disclosures of which are incorporated by reference herein.

FIELD OF THE INVENTION

The present disclosure relates to an implantable marker for use in surgical guidance; in particular an implantable marker having one or more ferromagnetic elements which are detectable by susceptometry using a probe which emits a magnetic field. The present disclosure also concerns a method of manufacturing such a marker.

BACKGROUND

Markers are used to guide surgeons to a region of interest during a surgical procedure, where the site of interest may not be physically visible or palpable; for example, a small tumour that needs to be excised. Suitably, such markers need to be deployable through a narrow gauge needle, e.g. 18 G to 12 G in order to reduce trauma to the patient. Typically, such markers are less than 10 mm in length, so as to be unobtrusive and to minimise trauma. The marker may be placed during a biopsy or other surgical procedure at a site of interest in the body; for example, a cancer lesion. The marker is placed under imaging guidance such as ultrasound or X-ray/mammography. During subsequent surgery, the marker is detected and localised with a handheld probe which provides audible, visual or other feedback to the surgeon to guide the surgery. Typically, the marker is excised along with the surrounding tissue.

A known approach is to use a marker containing a radioisotope such as iodine-125, which can be detected using a handheld gamma detection probe. However, use of radioactive materials is closely regulated, making it challenging to set up a radioactive seed programme in all but the largest academic hospital centres.

A different approach, which is exemplified by WO 2011/067576 A1, WO 2014/013235 A1 and WO 2013/140567 A1, uses magnetic fields and a ferromagnetic marker with high initial magnetic susceptibility. A handheld probe generates an alternating driving magnetic field ("sensing field"), which excites a magnetically responsive marker that produces a responding magnetic field, which can be detected by the probe using susceptometry. Suitably, the probe is configured to produce a sensing field having a strength at source of between about 0.2 mT and about 1.2 mT, giving rise to a field strength of between about 40 μT and about 400 μT within about 5 mm of the probe. This approach has been found to be highly effective for deeper sensing to localise a tumour, typically with a diameter of less than about 20 mm, and avoids the drawbacks of RF approaches. However, in an MRI setting using a much stronger magnetic field of, for example, 1.5 T or 3 T, this approach can lead to an unwanted artefact being generated as a result of the ferromagnetic material which is large compared to the marker itself and which may obfuscate the MRI image.

MRI is used to image lesions which are not visible on ultrasound or mammography for invasive breast cancer, and MRI monitoring is increasingly being used for evaluation of neoadjuvant therapy prior to surgical excision, allowing for the size for the tumours to be tracked after neoadjuvant therapy and prior to surgery. An MRI artefact of such a marker should not compromise the assessment by a healthcare professional of the size of the tumour, as a decrease in the size of the tumour would offer positive options in the management of a cancer patient. In this respect, breast cancer stages are typically evaluated using several criteria, such as the tumour size, whether the tumour has spread to the lymph nodes, and if the cancer has spread to other parts of the body (metastasis). Early stage cancers where breast conserving surgery using lumpectomy can be envisaged should preferably present a tumour size of 2 cm of less. Shashla (Neoadjuvant chemotherapy in breast cancers, September 2016, DOI: 10.1177/1745505716677139) indicates that smaller tumour size represents a good prognostic factor, and residual tumours of >2 cm are associated with higher rates of locoregional tumor recurrence after neoadjuvant chemotherapy. Koh et al. (Introduction of a New Staging System of Breast Cancer for Radiologists: An Emphasis on the Prognostic Stage, January 2019, DOI: 10.3348/kjr.2018.0231) indicate that tumours where the size is below 2 cm are classified as T1 and correspond to a cancer stage 1 or 2 which is typically when a breast conservation surgery can be envisaged. A larger tumour will more likely lead to more radical procedures, such as mastectomy. It is highly desirable therefore to be able to size the tumour under MRI when it exceeds 2 cm in diameter, enabling assessment of whether the tumour has shrunk to a size that would allow breast conservation surgery.

Ferromagnetic materials are well known for creating MRI distortions and these have been widely described in the scientific literature. For example, Hargreaves et al. (Metal Induced Artifacts in MRI, August 2017, DOI: 10.2214/AJR.11.7364) explain that some ferromagnetic materials may be safe for MRI but would still create significant artefacts. The artefact is predominantly generated by the component of the magnetic field generated by the ferromagnetic object (By) that is in the same direction as the main y-axis field produced by the MRI machine, as described in more detail below. The effect of By is to shift the local Larmor frequency of protons near the object, and if that shift is large enough, those protons will not appear in the correct slice in an x-z plane reconstructed by the MRI machine.

Options have been studied by Gao et al. (Reduction of artefact of metallic implant in magnetic resonance imaging by combining paramagnetic and diamagnetic materials, May 2010, DOI: 10.1063/1.3352582) for decreasing the size of MRI artefacts caused by metallic implants made of paramagnetic materials, such as a cylindrical hip joint and an aneurysm clip, by coating the metallic implant with a diamagnetic material. These options rely on the fact that paramagnetic and diamagnetic materials have magnetic susceptibilities of comparable magnitude so that the effect of a given volume of paramagnetic material can be cancelled by a similar volume of diamagnetic material. However, they are unpromising for use with implantable magnetic markers which comprise ferromagnetic materials having a susceptibility that is typically between 10 million and 1,000 million times greater in magnitude than that of diamagnetic materials.

Bismuth, a well-known diamagnetic material, has a bulk susceptibility of about $-1.66\times10^{-4}$, but is unsuitable for use in an implantable marker owing to toxicity concerns and difficulties in machining (as it is relatively soft and not malleable). Meanwhile, graphite is reported to have a bulk susceptibility of about $-0.16\times10^{-4}$.

There is therefore a need in the art for an implantable ferromagnetic marker with a good isotropy of sensing response, long sense range, while showing a small MRI artefact. The present disclosure seeks to provide an improved magnetic marker, with a reduced MRI artefact that overcomes, or at least alleviates, at least some of the above-mentioned drawbacks.

SUMMARY OF DISCLOSURE

According to a first aspect, there is provided an implantable marker for use in surgical guidance comprising one or more ferromagnetic elements formed of at least one ferromagnetic material and at least one diamagnetic element formed of at least one diamagnetic material; wherein the at least one diamagnetic material comprises graphite having a substantially isotropic grain structure (i.e. isotropic graphite).

The one or more ferromagnetic elements may be arranged in juxtaposition with the at least one diamagnetic element, meaning the diamagnetic and ferromagnetic elements are located adjacent one another in the marker. Surprisingly, it has been found that the presence of one or more ferromagnetic elements in close proximity to the at least one diamagnetic element appears to increase the apparent bulk susceptibility of the graphite. For instance, while graphite is reported in the literature to have a bulk susceptibility of about $-0.16\times10^{-4}$, it has been found that its apparent bulk susceptibility may be increased (made more negative) in the presence of the one or more ferromagnetic elements to about $-1.2\times10^{-4}$. Without wishing to be bound by any particular theory, it is thought that in the presence of a magnetic field, for example an MRI field of 1.5 T or more, the one or more ferromagnetic elements increase the field in the at least one diamagnetic element, giving rise to a stronger apparent bulk susceptibility. The surprising effect has been demonstrated in isotropic graphite, however other diamagnetic materials such as bismuth, and indeed non-isotropic graphites such as pyrolytic graphite, do not demonstrate the same enhancement effect.

Further, graphite having a substantially isotropic grain structure has a practically isotropic magnetic response which makes it suitable for use in an implantable marker, where the orientation of the marker within a body will inevitably vary from one procedure to another. Isotropic graphite demonstrates a high (negative) bulk susceptibility in all directions of observation. Using isotropic graphite consequently provides a more predictable reduction in marker artefact size (whatever the orientation of the marker).

In some embodiments, all or most of the diamagnetic material of the marker may comprise graphite having a substantially isotropic grain structure. Typically, there may be only one diamagnetic material. In other words, the diamagnetic element may be formed only of graphite having an isotropic grain structure (wherein the grains are substantially randomly oriented).

The inventors have found that graphite having a substantially isotropic grain structure has suitable magnetic properties for use as a diamagnetic material in the diamagnetic element of the marker. Use of graphite as a diamagnetic material has been found to allow the manufacture of a marker wherein the at least one diamagnetic element has a negative magnetic susceptibility large enough to produce a magnetic moment of sufficient amplitude in an MRI field to reduce materially (e.g. to below about 30 mm) the size of an MRI artefact caused by magnetisation of the one or more ferromagnetic elements which have sufficient initial permeability and are present in sufficient volume to be detectable under susceptometry with a useful detection range for surgery. In addition, graphite in its various forms tends to be biocompatible and easy to machine.

Suitable ferromagnetic materials have a high initial relative permeability and reach saturation of induction above a threshold applied field. For example, the at least one ferromagnetic material may have an initial relative permeability of at least about 1,000. In some embodiments, the ferromagnetic material may have an initial relative permeability of at least about 10,000, at least about 50,000 or at least about 70,000. In some embodiments, the ferromagnetic material may have an initial relative permeability of up to or even more than about 100,000.

Meanwhile, graphite has an initial relative permeability which is at least seven orders of magnitude lower than the initial relative permeability of the ferromagnetic material and does not saturate. In accordance with the present disclosure it has been found that the above-described properties of the materials may be advantageously utilised to provide an implantable marker in which, in a sensing field, the one or more ferromagnetic elements are substantially more strongly magnetised than the at least one diamagnetic element, for generating a responding magnetic field of sufficient magnitude to allow the marker to be detected by susceptometry in tissue using a handheld probe with a practically useful range; and in an MRI field, the one or more ferromagnetic elements are saturated, thereby limiting their magnetisation to their saturation induction, $B_S$, while the at least one diamagnetic element, whose magnetisation is not capped by saturation, has a degree of magnetisation which is sufficiently strong to offset all or at least a substantial proportion of the induced magnetisation of the one or more ferromagnetic elements, thereby minimising the size of the artefact produced by the marker; especially an MRI artefact produced in an MRI image on an x-z plane of an MRI scanner.

In a sensing field, therefore, the amplitude of the magnetic moment produced by the one or more ferromagnetic elements may be 1,000 to 1 million times greater than the magnetic moment produced by the at least one diamagnetic element.

It has been found that an implantable marker comprising graphite as a diamagnetic material displays a good reduction in marker MRI artefact size (for example in an MRI image on an x-z plane of an MRI scanner) and moreover may be manufactured to be suitably small.

The graphite may advantageously have a density in the range of about 1.2 to about 1.9 g/cm$^3$ or higher.

The graphite may have a bulk susceptibility which is relatively high compared to diamagnetic materials in general. Thus, the graphite may have a bulk (negative) susceptibility of at least about $-0.16\times10^{-4}$. In the marker of the present disclosure, in the presence of the one or more ferromagnetic elements, the graphite may have an apparent bulk (negative) susceptibility of magnitude more than about $0.9\times10^{-4}$, for example more than about $1\times10^{-4}$, e.g. about $1.2\times10^{-4}$. In some embodiments, the graphite may have a bulk (negative) susceptibility of magnitude about $1\times10^{-4}$ to about $3\times10^{-4}$. The graphite may advantageously be manufactured to have a bulk (negative) susceptibility in the above ranges.

Accordingly, the at least one diamagnetic element may have an bulk magnetic susceptibility that is sufficiently large to produce a magnetic moment of sufficient amplitude in an MRI field to reduce materially the size of an MRI artefact caused by magnetisation of the one or more ferromagnetic elements (for example in an MRI image on an x-z plane of an MRI scanner), preferably to less than 30 mm; even more preferably less than 20 mm.

Suitably, the graphite may be isostatically pressed graphite. Isostatically pressed graphite is graphite that has been formed by isostatic pressing and consequently has an isotropic grain structure (with substantially randomly oriented grains). This compares to other manufacturing techniques such as extrusion and compression moulding, which may cause an anisotropic grain structure. During the process, the raw material mixture is compressed into blocks in a so called Cold-Isostatic-Press. This technology can produce the most isotropic form of artificial graphite. Isostatically pressed graphite has a comparatively isotropic grain structure, high density, high strength and fine grain structure compared to other forms of graphite.

Isostatically pressed graphite per se is known generally, but not within the field of magnetic markers for surgical guidance. The desirable properties for isostatically pressed graphite have long been identified to be high thermal and chemical resistance, good thermal shock resistance, high electrical conductivity, high thermal conductivity, increasing strength with rising temperature, good corrosion resistance, high dimensional accuracy and high surface quality, and ease of machining for applications such as electrodes for electrical discharge machining, electrodes used in the manufacture of semiconductors and photovoltaic cells, moulds and components for glass casting and aluminium production and dies used in continuous casting of various metals and alloys. To date, isostatically pressed graphite has primarily been used for its mechanical and thermal properties. The present inventors have discovered that isostatically pressed graphite has useful magnetic properties which have not previously been realised and which are particularly suited to applications in the present field of surgical magnetic markers. In particular it has been discovered that isostatically pressed graphite provides a strong diamagnetic material.

Isostatically pressed graphite has surprisingly been found to have particularly suitable properties for use as a diamagnetic material in the diamagnetic element. In particular, it has been found to have a suitably high and isotropic magnetic susceptibility (wherein it has a comparable magnetic susceptibility along all axes). This provides a significant advantage over other forms of graphite, for example graphite formed by extrusion or compression moulding, wherein the anisotropic grain structure leads to a stronger magnetic susceptibility along an axis perpendicular to the grain orientation compared to an axis parallel to the grain direction. As one is unable to control the orientation of the implanted marker in the clinical setting and therefore the marker artefact within the patient, isotropic magnetic susceptibility is desirable because it leads to a reduction in marker artefact size in an MRI image for example in an x-z plane, or in a y-plane (the direction of the field) of an MRI scanner, when used to cancel the effect of a ferromagnetic marker. The effect is present regardless of the orientation of the implanted marker. Thus isostatically pressed graphite therefore provides advantages when used as a diamagnetic material in the diamagnetic element as compared to other, anisotropic, forms of graphite and other diamagnetic materials in general. In addition, isostatically pressed graphite is easy to fabricate and machine, and can be non-toxic or biocompatible.

The isostatically pressed graphite may have a bulk susceptibility of at least about $-1.2\times10^{-4}$. Surprisingly, it has been found that isostatically pressed graphite may have a bulk (negative) susceptibility of magnitude about $1.2\times10^{-4}$ and offer good isotropic susceptibility, whilst being inexpensive and readily machinable into shape, and have good biocompatibility characteristics. It is believed that the especially good isotropic susceptibility of isostatically pressed graphite may result from its isotropic grain structure (wherein the graphite is produced from a plurality of randomly oriented grains).

Suitably, the graphite should have a high purity, for example containing fewer than 500 ppm, for example fewer than 300 ppm, for example fewer than 50 ppm of impurities. Isostatically pressed graphite is conveniently produceable in suitable grades with fewer than 5 ppm of impurities. The isostatically pressed graphite may contain more than 99.9% carbon. A higher purity has been found to advantageously increase magnetic susceptibility as it permits a larger amount of diamagnetic material for a given volume hence increasing the diamagnetic response. Moreover, if the impurities have a paramagnetic susceptibility then removing them avoids diminishing the diamagnetic response. In a further possible effect, it is thought that a higher purity may permit formation of better, more suitable, crystal structures.

The inventors have further appreciated that high density graphite may advantageously provide a stronger diamagnetic effect in a given volume, due to the increased amount of diamagnetic material present. In other words, a diamagnetic element containing high density graphite may provide an increased diamagnetic artefact size compared to a lower density graphite, leading to a further reduction in overall marker artefact size. Correspondingly, it has been found that low porosity graphite is advantageous for similar reasons of maximising the amount of diamagnetic material present in the given volume.

Thus, in some embodiments, the graphite may have a density of at least about 1.75 g/cm$^{-3}$, e.g. about 1.85 g/cm$^{-3}$. In some embodiments, the graphite may have a density of up to about 1.95 g/cm$^{-3}$. A density in the range of about 1.75 g/cm$^{-3}$ to about 1.95 g/cm$^{-3}$ implies a low porosity (in the region of 7-17%). The diamagnetic effect may advantageously be increased for densities above about 1.8 g/cm$^{-3}$, and correspondingly the diamagnetic artefact size is increased (to better offset the ferromagnetic artefact size, and reduce the consequent marker artefact size).

The graphite may have a porosity of less than 20%, more preferably less than 15%.

Advantageously, the composition of the graphite can be optimised to produce a material grade which optimally reduces the MRI artefact of the magnetic marker by increasing the diamagnetic effect of the graphite comprised in the diamagnetic element. For example, the graphite grade may be an ultra-high purity graphite (containing fewer than 5 ppm of impurities), with a high density (e.g. above 1.8 g/cm$^{-3}$) and a corresponding low porosity (e.g. of less than 15%).

The isostatically pressed graphite may be heat treated graphite. The isostatically pressed graphite may be processed at a high temperature, for example in excess of about 2,000° C., more preferably in excess of about 2,200° C. In particular, the temperature of the graphite may be raised during or subsequent to pressing. Heat treatment at high temperatures has advantageously been found to increase the magnetic susceptibility of the graphite, thereby reducing the size of the marker artefact in the MRI field. It is thought that heat treatment may beneficially improve the graphite grain structure (for example by increasing the grain size) and purity.

The isostatically pressed graphite may have a fine grain structure. In other words, the isostatically pressed graphite may have a finer grain structure than that of graphite produced by other methods such as extrusion or compression moulding.

Thus, the isostatically pressed graphite may have a grain size of less than 20 microns, for example less than 15 microns, for example less than 10 microns. The inventors have appreciated that a finer grain structure may result in a smaller size of marker artefact in the MRI field; for example as taken in an x-z plane, as defined by the MRI machine in which the principal magnetic field is oriented along the y-axis. It is thought that a smaller grain size together with the isotropic grain structure of isostatically pressed graphite may enable good isotropic susceptibility (for example at least in part owing to lower freedom of movement of electrons within the graphite material). For example, isostatically pressed graphite may have a ratio of magnetic anisotropy of about 7 or less.

The at least one diamagnetic element may be configured and arranged, for example as disclosed above, to produce an artefact in the MRI field which has a size and shape that matches the artefact size and shape of an artefact produced by the one or more ferromagnetic elements to a sufficient degree; for example as taken in an x-z plane, defined by the MRI machine in which the principal magnetic field is oriented along they-axis, to reduce the maximum dimension of the artefact created by the marker to less than about 30 mm.

Suitably, the total volume of diamagnetic material in the marker may be about 100 to about 10,000 times greater than the total volume of ferromagnetic material, for example about 900 times greater. Suitably, the at least one diamagnetic element may have a total volume that is about 100 to 10,000 times greater than the volume of the one or more ferromagnetic elements; preferably about 500-3,000 times greater, for example about 900 times greater.

The amount of diamagnetic material may be selected to minimise the net magnetisation of the marker in an MRI field, without "over-compensating" for the ferromagnetic material and thereby creating an unacceptably large artefact resulting from the diamagnetic material. MRI machines are available with different field strengths; typically in the range of about 0.5 T to about 3 T (although fields of up to about 7 T are known for clinical application). In some embodiments of the present disclosure, therefore, the marker may comprise relative amounts of ferromagnetic and diamagnetic materials which together produce an acceptably small artefact at two or more different MRI field strengths; particularly within the range of about 0.5-10 T, preferably about 1-5 T; for example at about 1.5 T and about 3 T. For example, the marker may comprise amounts of ferromagnetic and diamagnetic materials which together have approximately no net magnetisation at one MRI field strength, while having a net magnetisation at another MRI field strength which still gives rise to an acceptably small artefact. Alternatively, the marker may comprise relative amounts of ferromagnetic and diamagnetic materials which are optimised to give rise to acceptably small artefacts at two or more different MRI field strengths. By "acceptably small" herein is meant less than about 30 mm, preferably less than about 20 mm; particularly in an MRI image on an x-z plane of an MRI machine.

Suitably, in an MRI field, the opposing magnetic moment generated by the one or more ferromagnetic elements or, respectively, the at least one diamagnetic element may have an amplitude of at least 25%, preferably at least 50%, of the amplitude of the magnetic moment produced by the at least one diamagnetic element or, respectively, the one or more ferromagnetic elements; whereby the artefact produced by the marker in the MRI field may be less than about 30 mm in its longest dimension; preferably less than about 20 mm.

The one or more ferromagnetic elements and the at least one diamagnetic element may be co-located. By "co-located" herein is meant that the one or more ferromagnetic elements and the at least one diamagnetic element are configured and arranged to occupy and extend across substantially the same space (or volume) in the marker.

Further, the at least one diamagnetic material may have an apparent bulk susceptibility such that in an MRI field the one or more ferromagnetic elements and the at least one diamagnetic element generate opposing magnetic moments, the amplitude of the smaller one of which is at least about 25% of the amplitude of the larger one. As disclosed herein, a sufficient volume of diamagnetic material may be used to produce a magnetic moment which has an amplitude that is within at least 75% of the amplitude of the opposing magnetic moment generated by the one or more ferromagnetic elements, i.e. the magnetic moment generated by the diamagnetic material has an amplitude that is within a range of about 25% to about 175% of the amplitude of the opposing magnetic moment generated by the one or more ferromagnetic elements.

In some embodiments, the marker may comprise relative amounts of ferromagnetic and diamagnetic materials such that the magnetic moments generated by at least one of them under at least two different MRI fields are each separately within about 75% of corresponding magnetic moments generated by other; preferably within about 50%. Thus, in some embodiments, the magnetic moments generated by the diamagnetic material may have amplitudes under at least two different MRI fields that are each separately within a range of about 25% to about 175% of corresponding amplitudes of the opposing magnetic moments generated by the one or more ferromagnetic elements; preferably within the range of about 50% to about 150%. Suitably, therefore, the magnetic moments produced by the at least one diamagnetic element under at least two different MRI fields may each separately be at least 25% or more of the corresponding magnetic moments produced by the one or more ferromagnetic elements. In this manner, the amounts of ferromagnetic and diamagnetic material in the marker may be optimised to target an acceptably small artefact under two or more different MRI fields; particularly in the range about 0.5-10 T, preferably 1-5 T, e.g. at 1.5 T and 3 T.

As described above, the sensing field may suitably have a strength of between about 0.1 mT and about 2.0 mT at source; preferably about 0.2 mT and about 1.2 mT, giving rise to a field strength of between about 40 μT and about 400 μT within about 5 mm of the probe. Conveniently, this may allow the marker to be detected at a range of up to about 50 mm, about 60 mm, about 70 mm or even up to about 80 mm from the probe.

The MRI field may typically have a strength of at least 1.5 T. Suitably, the one or more ferromagnetic elements may be configured and arranged, as disclosed herein, to generate a responding magnetic field of sufficient magnitude to allow the marker to be detected in tissue with a handheld probe in a sensing field at least 200,000 times weaker than an MRI field; preferably at least 400,000 times weaker and, in some embodiments, up to 800,000 or more times weaker.

The one or more ferromagnetic elements may have a saturation induction $B_S$ of less than about 1.5 T; preferably less than about 1 T. Thus, in some embodiments, the one or more ferromagnetic elements may be configured and arranged, as disclosed herein, to generate a responding magnetic field of sufficient magnitude to allow the marker to be detected in tissue with a handheld probe in a sensing field at least 1,000 times weaker than $B_S$ of the one or more ferromagnetic elements.

In some embodiments, the one or more ferromagnetic elements may have a total volume of less than about $1\times10^{-10}$ $m^3$; preferably less than about $5\times10^{-11}$ $m^3$, $3\times10^{-11}$ $m^3$, or $1\times10^{-11}$ $m^3$, for example $6\times10^{-12}$ $m^3$. In some embodiments, the one or more ferromagnetic elements may have a total volume which is as low as about $1\times10^{-12}$ $m^3$. Typically, the total volume of the at least one diamagnetic element may be between about $1\times10^{-9}$ $m^3$ and $1.5\times10^{-7}$ $m^3$. Advantageously, it has been found that a marker comprising volumes of ferromagnetic and diamagnetic materials within these ranges may be presented in a form having dimensions which are suitable for implantation, typically by injection. For example, the marker may have a width in the range of about 0.8 mm to about 3 mm; preferably about 1-1.5 mm. The marker may have a length of about 2-10 mm, for example 5 mm.

The implantable marker may comprise one or more pieces of a ferromagnetic material. Said one or more pieces may comprise one or more wires or strips. Suitably, therefore the wires or strips may have a total length to diameter ratio, or a ratio of length to square root of cross-sectional area, of at least about 50. Suitably the wires or strips may have a length in the range 30-40 mm, for example about 36 mm.

In some embodiments, the one or more ferromagnetic elements may have a total length to diameter (or square root of cross-sectional area) ratio of more than 100, more than 500, more than 1000 or more than 2000, for example about 2400. In some embodiments, the one or more ferromagnetic elements may have a total length to diameter (or square root of cross-sectional area) ratio of more than 3000.

It has been found that by increasing the length-to-diameter (or root of cross-sectional area) ratio of the at least one piece of ferromagnetic material, the sensing response of the marker may be improved, thereby allowing a smaller volume of ferromagnetic material to be used for a given responding field, which gives rise to a smaller MRI artefact.

In some embodiments, the one or more pieces of a ferromagnetic material may have a total volume of less than $1\times10^{-10}$ $m^3$, preferably less than $5\times10^{-11}$ $m^3$, for example less than $1\times10^{-11}$ $m^3$, for example about $5\times10^{-12}$ $m^3$.

Suitably, the one or more pieces of ferromagnetic material may be configured to optimise the isotropy of the responding field generated by the marker. The one or more ferromagnetic elements of the marker may be configured to achieve a ratio of magnetic flux anisotropy of less than 7, preferably less than 5. Suitably, the one or more ferromagnetic elements of the marker of the present disclosure may be configured as disclosed herein; for example as a helix or a multiple helix.

Those skilled in the art will appreciate that to derive maximal benefit from the use of a sufficient volume of diamagnetic material that has a magnetisation in an MRI field that is comparable with the magnetisation of the one or more ferromagnetic elements, the at least one diamagnetic element may advantageously be configured and arranged to create an artefact in an MRI field that has a similar shape, but opposite polarity, to the artefact created by the one or more ferromagnetic elements. Suitable configurations and arrangements of the ferromagnetic and diamagnetic elements may be determined empirically by using suitable mathematical modeling or computer-aided engineering (CAE) software such, for example, as that which is available from Comsol AB (Sweden) under the trade mark COMSOL Multiphysics® or from Ansys, Inc. (Canonsburg, PA) under the trade mark ANSYS®, to produce simulated contour maps of the respective artefacts that would be produced by the one or more ferromagnetic elements and at least one diamagnetic element in an MRI field and iteratively adjusting the configuration and arrangement of the elements until the contour maps substantially match. Suitably, the at least one diamagnetic element may be configured as disclosed herein; for example as a cylinder. The one or more ferromagnetic elements may, in some implementations of the disclosure, be wrapped around an outer surface of the cylinder as a helix or multiple helices.

The one or more ferromagnetic elements and at least one diamagnetic element may comprise respective volumes of ferromagnetic and diamagnetic materials that are selected such that in a sensing field, the one or more ferromagnetic elements are substantially more strongly magnetised than the at least one diamagnetic element, for generating a responding magnetic field of sufficient magnitude to allow the marker to be detected in tissue using a handheld susceptometry probe. In the MRI field, the at least one diamagnetic element has a degree of magnetisation which is sufficiently strong to offset at least a substantial proportion of the magnetisation of the one or more ferromagnetic elements, thereby minimising the size of the artefact produced by the marker, as disclosed herein.

Suitably, the one or more ferromagnetic elements may be configured and arranged to maximise the strength and isotropy of a responding field generated in response to the sensing field.

According to a second aspect, there is provided an implantable marker comprising one or more wires or strips formed from a ferromagnetic material, the wires or strips being disposed around or extending axially through a diamagnetic core; wherein the diamagnetic core comprises at least one body of isostatically pressed graphite, having an apparent bulk susceptibility of at least about $-1.2\times10^{-4}$. As such, the one or more ferromagnetic wires or strips are arranged to be juxtaposed the diamagnetic core. The one or more ferromagnetic wires or strips may be arranged to be co-located with the diamagnetic core, for example extending along the full length of the diamagnetic core.

Suitably, the body of isostatically pressed graphite may be substantially cylindrical.

In some embodiments, the wires or strips formed from a ferromagnetic material may be generally linear. The wires or strips may be disposed around the outside of the diamagnetic core.

In some embodiments, the implantable marker may comprise one or more helical coils of wire formed from a ferromagnetic material disposed around the diamagnetic core.

Suitably, the implantable marker may comprise a single helical coil of wire disposed around the outside of the diamagnetic core. Alternatively, the implantable marker may comprise two, three, four or more coils of wires arranged as a multiple (e.g. triple) helix around the outside of the diamagnetic core.

The diamagnetic core may have a diameter of about 1 mm, for example about 1.2 mm, and a length in the range 4-9 mm, for example about 5 mm. The total marker length may correspondingly have a length in the range 4-9 mm, for example about 5 mm.

The wires or strips may each have a diameter of about 15 μm or less.

According to a third aspect of the present disclosure, there is provided a method of manufacturing an implantable magnetic marker for use in surgery, the method comprising the steps of: forming one or more ferromagnetic elements from at least one ferromagnetic material; forming at least one diamagnetic element, wherein at least one diamagnetic element comprises graphite having a substantially isotropic grain structure, and thereafter assembling the one or more ferromagnetic elements and the at least one diamagnetic element such that the one or more ferromagnetic elements are juxtaposed the at least one diamagnetic element; wherein the one or more ferromagnetic elements and the at least one diamagnetic element are configured and arranged to produce mutually opposing magnetic moments in the presence of an applied magnetic field. The implantable marker may be the implantable marker according to either the first or second aspects of the present disclosure.

The one or more ferromagnetic elements and the at least one diamagnetic element may be assembled such that the at least one diamagnetic element is co-located with the one or more ferromagnetic elements, for example extending across the same length or volume of the marker.

The graphite may be isostatically pressed graphite, and the method may include the step of performing an isostatic pressing process to produce the isostatically pressed graphite. Advantageously, such a method provides an isotropic grain structure in the graphite i.e. the method yields physical properties of the resulting material which are isotropic. Isostatically pressed graphite manufactured as such advantageously has a comparatively high density, high strength and fine grain structure.

The method may further include the step of heat treating the graphite. Heat treatment may increase the magnetic susceptibility of the isostatically pressed graphite (as it aids the formation of the carbon-carbon structure). Heat treatment may increase the density of the isostatically pressed graphite.

Heat treatment may reduce the level of impurities in the isostatically pressed graphite. The heat treating step may be carried out simultaneously or subsequent to pressing or extruding the graphite. The heat treating step may be carried out at a temperature in excess of 2,200 degrees Celcius.

According to a fourth aspect, the present disclosure comprehends use of graphite having a substantially isotropic grain structure in an implantable marker comprising one or more ferromagnetic elements for reducing the magnetic moment of the marker in an MRI field, thereby to minimise the size of an artefact created by the marker. Suitably, the present disclosure may comprehend use of graphite having a substantially isotropic grain structure in at least one diamagnetic element juxtaposed one or more ferromagnetic elements in the implantable marker. For example, the at least one diamagnetic element may be co-located with the one or more ferromagnetic elements in the implantable marker, meaning that the one or more ferromagnetic elements and the at least one diamagnetic element are configured and arranged to occupy and extend across substantially the same space (or volume) in the marker.

Use of graphite as a diamagnetic material (typically the only or predominant diamagnetic material) in the diamagnetic element has been found to be particularly effective at countering the effect of a strong ferromagnetic susceptibility marker, leading to a significantly reduced marker artefact size. Graphite can be manufactured to have properties, for example a density, leading to a desired, comparatively high, magnetic susceptibility. When the graphite is isostatically pressed graphite, it advantageously has an isotropic magnetic susceptibility, leading to a better reduction in the marker artefact size in any given plane.

According to a fifth aspect, there is provided a detection system for locating an implantable marker, the system comprising: an implantable marker according to the first or second aspects; at least one drive coil arranged to excite the implantable marker with an alternating magnetic field and at least one sense coil arranged to detect a signal received from the excited implantable marker; a magnetic field generator arranged to drive an alternating magnetic field through the at least one drive coil; and at least one detector arranged to receive the signal from the sense coil and detect one or more harmonics of the drive frequency in the received signal.

It will be appreciated that features described herein in relation to one aspect of the present disclosure may be incorporated into other aspects of the present disclosure. For example, the method of the disclosure may incorporate features described with reference to the marker of the disclosure and vice versa.

DESCRIPTION OF THE DRAWINGS

Following is a description by way of example only with reference to the accompanying drawings of embodiments of the present disclosure.

In the drawings:

FIG. 1(*b*) is another schematic side view of an MRI scanner which shows how image slices are cut up along the y-axis and indicates the orientation of the x, y and z axes.

FIG. 2(*a*) is a hysteresis curve 1 showing magnetisation as a function of magnetic field, H, for a typical ferromagnetic material;

FIG. 2(*b*) is a similar hysteresis curve to FIG. 2(*a*) showing magnetic flux, B, as a function of magnetic field, H, for atypical ferromagnetic material;

FIG. 2(*c*) is a schematic diagram showing direction of the magnetic moment generated in a ferromagnetic material when subject to an applied magnetic field H;

FIG. 3(*b*) is a schematic diagram showing direction of the magnetic moment generated in a diamagnetic material when subject to an applied magnetic field;

FIG. 6(*b*) is a comparative contour map of magnetic flux density B in an x-z plane of the MRI scanner, which shows how B deviates from an MRI field $B_0$ as a result of the presence in the field of the same configuration of ferromagnetic wires as shown in FIG. 5, but in the absence of the diamagnetic core.

FIG. 10(*b*) is a comparative contour map of magnetic flux density B in an x-z plane of the MRI scanner, which shows how B deviates from an MRI field $B_0$ as a result of the presence in the field of the same configuration of ferromagnetic wires as shown in FIG. 9, but in the absence of a diamagnetic core.

FIG. 12(*b*) is a comparative contour map of magnetic flux density B in an x-z plane of the MRI scanner, which shows how B deviates from an MRI field $B_0$ as a result of the presence in the field of the same configuration of ferromagnetic wires as shown in FIG. 10, but in the absence of the diamagnetic core;

DEFINITIONS

Figure 1A:
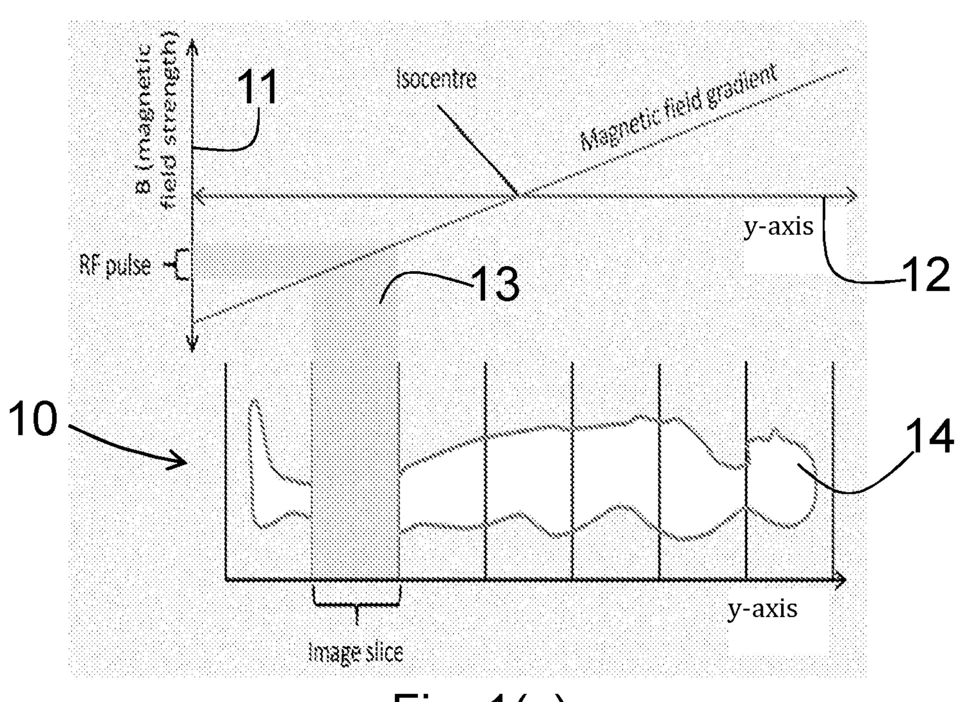
FIG. 1(*a*) is a schematic side view of a person lying in an MRI scanner, which indicates the field B gradient on ay-axis of a main magnetic field.

Isotropic graphite, is graphite having a substantially isotropic grain structure;

Isostatically pressed graphite, is isotropic graphite that has been formed by isostatic pressing;

Magnetic flux density, B, is a vector field measuring the strength and direction of the magnetic field around a magnet or an electric current;

Magnetic field strength, or the magnetising field, H, is a vector field that describes the magnetic influence on moving electric charges, electric currents, and magnetic materials;

Magnetisation, or magnetic polarisation, M, is a vector field that expresses the density of permanent or induced magnetic dipole moments in a magnetic material;

Saturation of induction is the state reached when an increase in applied external magnetic field, H, cannot increase the magnetisation, M, of the material further. In this state, the total magnetic flux density that results is called the saturation induction, $B_S$, and the magnetisation is the saturation magnetisation, $M_S$;

Magnetic susceptibility, $\chi$, is a measure of how much a material will become magnetised in an applied magnetic field, defined as $\chi$=M/H;

Bulk susceptibility, is a measure of the magnetic susceptibility of a material in its bulk shape when placed in a magnetic field;

Apparent bulk (diamagnetic) susceptibility, is a measure of the magnetic susceptibility of a diamagnetic material in its bulk shape when placed in a magnetic field in the presence of one or more shaped ferromagnetic materials;

Magnetic permeability, $\mu$, is the measure of a material's resistance against the formation of a magnetic field, defined as $\mu$=B/H;

Relative magnetic permeability ($\mu_r$) is the ratio of magnetic permeability to the permeability of free space ($\mu_0$); that is $\mu_r=\mu/\mu_0$. It is related to y by the equation $\mu_r=1+\chi$;

Initial susceptibility ($\mu_1$) is a measure of how much a material of infinite extent will become magnetised in a small applied magnetic field. It is defined as $\chi_i$=M/H for small H (e.g. less than 0.01 mT), or equivalently $$\chi_i = \left.\frac{\partial M}{\partial H}\right|_{H=0};$$

Apparent susceptibility, is a measure of the magnetic susceptibility of a material having a specific geometry when placed in a magnetic field;

Apparent initial susceptibility ($\times_{app}$), also known as effective susceptibility, is the initial susceptibility for a material of specific geometry in a small applied magnetic field. That is, it is $\chi_i$ after taking into account the demagnetisation factor;

Initial relative magnetic permeability ($\mu_{r,i}$) is the value of $\mu_r$ for small H, and is related to the initial susceptibility by $\mu_{r,i}=1+\chi_i$;

Apparent relative magnetic permeability ($\mu_{app}$) is the relative magnetic permeability of a material of specific geometry. That is, it is $\mu_r$ after taking into account the demagnetisation factor.

A ferromagnetic material has a variable permeability, $\mu$, that increases relative to the magnetic field and up to a maximum. Many ferromagnetic materials have a maximum permeability that can exceed 100,000;

A paramagnetic material has a constant magnetic permeability, $\mu$, slightly greater than 1;

A diamagnetic material has a constant magnetic permeability, $\mu$, slightly less than 1. Diamagnetism causes a repulsive effect by creating a small magnetic field in opposition to an externally applied field.

Coercivity is the magnetising field, H, needed to demagnetise a magnetic material completely;

Hard magnetic materials, or permanent magnets, have a high coercivity;

Soft magnetic materials have a low magnetic coercivity, and therefore are easily magnetised and demagnetised;

Demagnetising field, or stray field, is the magnetic field, H, inside the magnet generated by the magnetisation, M, of a magnetic material. It gives rise to shape anisotropy in ferromagnets with a single magnetic domain and to magnetic domains in larger ferromagnets;

Demagnetisation factor is a quantity that must be used in order to determine the demagnetising field. An arbitrarily shaped magnetic object has a total magnetic field that varies with location inside the object and can be complicated to calculate. This makes it difficult to determine the magnetic properties of a material, such as, for instance, how the magnetisation of a material varies with the magnetic field;

An anisotropic material is a material which has different properties depending on the direction of observation. For example, the material properties such as thermal and electrical conductivity of graphene may vary significantly depending on whether they are measured in a direction parallel to the surface of the graphene planes, or a direction perpendicular to the surface of the planes.

An isotropic material is a material which has the same properties whichever the direction of observation. For example, the material properties of isotropic graphite (such as isostatically pressed graphite) are broadly the same whichever the direction of measurement. Structurally, isotropic graphite (i.e. graphite having an isotropic grain structure) is substantially homogenous.

Figure 1B:
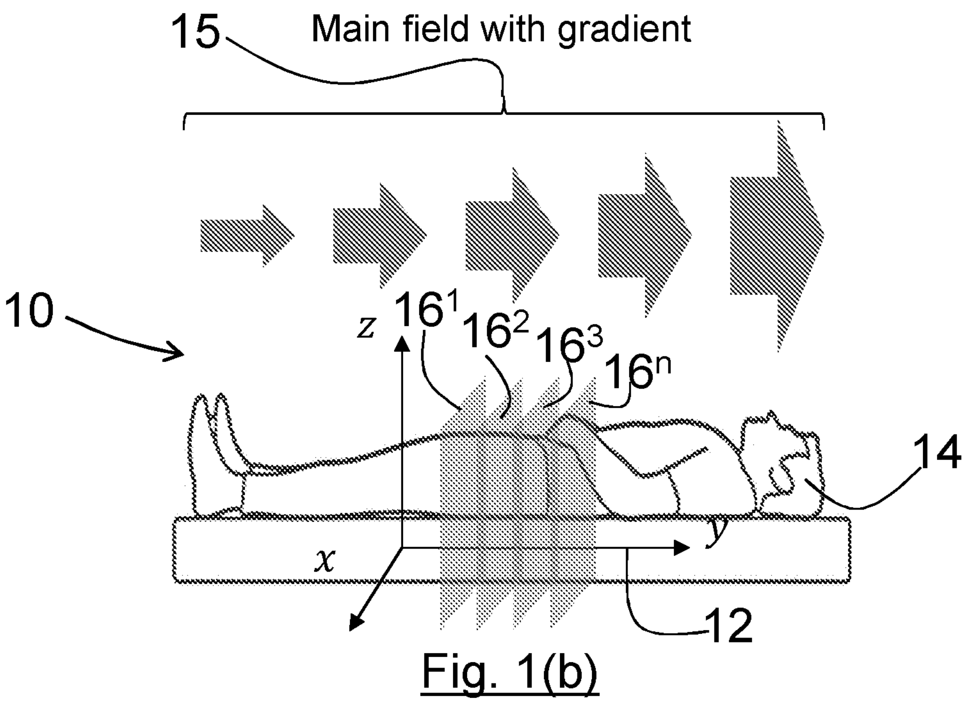

Magnetic anisotropy describes the variation of magnetic properties depending on the material orientation;

Magnetic anisotropy ratio is the ratio of the strongest to weakest magnetic signals produced by a marker at a constant distance at different orientations of the marker relative to a probe;

The magnetic moment is the magnetic strength and orientation of a magnet or other object that produces a magnetic field;

The magnetic dipole moment is a vector quantity associated with the magnetic properties of electric current loops;

Magnetic Resonance Imaging (MRI) is a non-invasive imaging technology that produces three dimensional detailed anatomical images. A typical MRI scanner 10 is illustrated schematically in FIGS. 1(*a*) and 1(*b*). A uniform main magnetic field 11, $B_0$, is aligned with a longitudinal y-axis 12 of the scanner. An RF pulse 13 $B_1$ is applied to perturb momentarily the net magnetisation M of atomic nuclei within the tissue of a patient 14 who lies within the scanner, as shown in FIG. 1(*a*). This RF excitation tips the magnetisation transiently away from the y-axis (i.e. parallel to $B_0$, where signal cannot be detected) to a transverse x-z plane (i.e. orthogonal to the y-axis), where it can be detected by suitable receiver coils. After the RF pulse is turned off, the magnetisation of the atoms relaxes and exhibits precession as it returns to its thermal equilibrium configuration. It is possible to detect the magnetisation because the transverse component of processing magnetisation induces an electromotive force in the receiver coils. This is detected as an NMR signal. The received signal is spatially encoded by the application of magnetic field gradients 15 which are superimposed on the main magnetic field as shown in FIG. 1(*b*).

MRI metal artefacts occur at interfaces of tissues and metal with different magnetic susceptibilities which cause local magnetic fields to distort the external magnetic field. This distortion changes the precession frequency in the tissue leading to spatial mismapping of information. $B_{crit}$ is defined as a critical change in magnetic flux B in the direction of the main field produced by an MRI machine at which an artefact is produced, which is caused by the metal, such that a voxel is mapped to an incorrect slice imaged by the MRI machine. In a typical MRI machine of the kind illustrated in FIGS. 1(*a*) and 1(*b*), the main field is aligned with ay-axis 12 and the slices 16$^1$, 16$^2$, 16$^3$, . . . 16$^n$ are respective x-z planes, orthogonal to the main y-axis 12. Accordingly, artefacts in an MRI image are generally artefacts in an x-z plane.

DETAILED DESCRIPTION

It is an object of the present disclosure to provide an implantable marker comprising one or more ferromagnetic elements, which generates a detectable response magnetic field at a probe when subjected to a driving magnetic field emitted by a handheld probe, and which produces a minimally sized artefact when subjected to a much stronger magnetic field in an MRI scanner; particularly in an x-z plane of the scanner. Suitably, the marker should be detectable using susceptometry.

In one embodiment, therefore, the present disclosure provides an implantable susceptometry marker for use in surgical guidance. The implantable marker comprises one or more ferromagnetic elements and at least one diamagnetic element. The one or more ferromagnetic elements and at least one diamagnetic element comprise respective amounts of ferromagnetic and diamagnetic materials such that, in a sensing field of less than about 0.5 mT (at source), the one or more ferromagnetic elements are substantially more strongly magnetised than the at least one diamagnetic element, for generating a responding magnetic field of sufficient magnitude to allow the marker to be detected in tissue using a handheld probe; and in an MRI field of 0.5 T or more, typically 1.5 T or more, the at least one diamagnetic element has a degree of magnetisation which is sufficiently strong to counteract at least a substantial proportion of the induced magnetisation of the one or more ferromagnetic elements. In this way, the marker of the present invention may produce a smaller MRI artefact than would a marker comprising the identical amount of ferromagnetic material without any diamagnetic material. Thus, for a given volume of ferromagnetic material, the size of the MRI artefact may be reduced to an acceptable size. As described in more detail below, the one or more ferromagnetic elements may advantageously comprise a total volume of ferromagnetic material of less than about $1\times10^{-10}$ $m^3$. In some embodiments, the total volume of the one or more pieces of ferromagnetic material may be less than $5\times10^{-11}$ $m^3$. In some embodiments, the total volume of the one or more pieces of ferromagnetic material may be less than about $3\times10^{-11}$ $m^3$, or less than about $1\times10^{-12}$ $m^3$. In some embodiments, the one or more ferromagnetic elements may have a total volume as low as about $1\times10^{-12}$ $m^3$. Thus, in some embodiments, the implantable marker may comprise between about $1\times10^{-12}$ $m^3$ and $1\times10^{-10}$ $m^3$ of ferromagnetic material.

In order to maximise its or their magnetisation in a sensing field, the one or more ferromagnetic elements may have a total length to diameter (or square root of their cross-sectional area) ratio of at least about 50, as disclosed in the United Kingdom patent application no. 2115827.4, the contents of which are incorporated herein by reference. Thus, in some embodiments, the length to diameter (or square root of their cross-sectional area) ratio of the one or more pieces of ferromagnetic material may be at least about 100, at least about 200, at least about 300, at least about 400 or at least about 500. In some embodiments, the length to diameter (or square root of their cross-sectional area) ratio of the one or more pieces of ferromagnetic material may be more than 1000, more than 2000 or more than 3000.

By way of example, the one or more pieces of ferromagnetic material may have a total length of about 36 mm and a diameter of about 15 μm. In such an example, the total length to diameter ratio of the one or more pieces of ferromagnetic material may be approximately 2400. The volume may be approximately $6\times10^{-12}$ $m^3$.

In some embodiments, the marker may comprise a wire or strip of ferromagnetic material having a length of at least about 3 mm, about 6 mm, about 10 mm, about 30 mm, 50 mm or about 100 mm long. A wire may have a diameter less than about 100 μm, or less than or equal to about 50 μm, about 30 μm, about 15 μm or about 10 μm. The marker may comprise a wire or strip of ferromagnetic material having a length of no more than about 3 mm, about 6 mm, about 10 mm, about 30 mm, about 50 mm or about 100 mm long. Suitably, the wire or strip may be formed into one or more pieces, as described herein.

Suitably, the ferromagnetic material may have an initial relative permeability of at least about 1,000. In some embodiments, the ferromagnetic material may have an initial relative permeability of at least about 10,000, at least about 50,000 or at least about 70,000. In some embodiments, the ferromagnetic material may have an initial relative permeability of up to or even more than about 100,000.

Further, as described below, the ferromagnetic material may have a saturation induction that is weaker than a typical MRI field. Suitably, therefore, the ferromagnetic material may have a saturation induction $B_S$ of less than about 1.5 T; preferably less than about 1.0 T; more preferably less than about 0.7 T.

The at least one diamagnetic element may suitably comprise a total volume of diamagnetic material that is between about 100-10,000 times greater than the total volume of the ferromagnetic material of the one or more ferromagnetic elements; preferably about 500-3,000 times greater; e.g. about 950-1,050 times greater. Thus, the at least one diamagnetic element may have a total volume of between about $1\times10^{-9}$ $m^3$ and about $1.5\times10^{-7}$ $m^3$. By selecting respective amounts of ferromagnetic and diamagnetic material within these ratios and/or volumes, and by virtue of saturation of induction of the ferromagnetic material in an MRI field, the amplitudes of the opposing magnetic moments generated by the one or more ferromagnetic elements and at least one diamagnetic element in an MRI field may be of the same order of magnitude. Preferably, the amplitude of a smaller one of the magnetic moments generated in an MRI field by the one or more ferromagnetic elements, or at least one diamagnetic element, may be at least 25%, preferably at least 50%, of the amplitude of a larger one of the magnetic moments produced by the at least one diamagnetic element, or respectively one or more ferromagnetic elements. In this way, the artefact size of the marker in an MRI field may be acceptable, i.e. less than about 30 mm in its longest dimension; preferably less than about 20 mm; particularly in an x-z plane of an MRI scanner as defined herein. Further, the total volume of ferromagnetic and diamagnetic material allows a marker to be manufactured which is sufficiently small as to be deployable through a narrow gauge needle, e.g. 18 G to 12 G.

The one or more ferromagnetic elements and at least one diamagnetic element may suitably be configured and arranged to produce mutually opposing magnetic moments in the presence of an applied magnetic field. In particular, when the marker is placed in an applied magnetic field, H, the one or more ferromagnetic elements produce a magnetic moment, $m_{ferromagnet}$, and the at least one diamagnetic element produces an opposing magnetic moment, $m_{diamagnet}$. The net magnetic moment of the marker, $m_{total}$, is thus given by $m_{total}=m_{ferromagnet}-m_{diamagnet}$. In a sensing field of less than about 0.5 mT (at source), the net magnetic flux produced by the marker determines the strength of the signal generated by the marker. In an MRI field, the magnetic flux produced by the marker impacts the size of an artefact generated in an MRI image.

As those skilled in the art will be aware, an MRI magnetic field may typically have a strength of between 0.5 T and 10 T or more; particularly between about 1.5 T and 7 T.

In the field of the present disclosure, a handheld susceptibility probe may be used by a surgeon to detect and localise the marker after implantation. Suitably, the probe may be a probe as described in WO 2014/140566 A1, the contents of which are incorporated herein by reference; for example a Sentimag™ probe, which is commercially available from Endomagnetics Ltd, UK.

The probe may produce a sensing field having a strength at source of between about 0.1 mT and about 2.0 mT, preferably between about 0.2 mT and about 1.2 mT, e.g. about 0.3 mT. This may give rise to a field strength of between about 25 μT and about 500 μT, preferably about 40 μT and about 400 μT, within about 5 mm of the probe, which may be at least 1,000 times weaker than $B_S$ of the one or more ferromagnetic elements. Typically, the sensing field may be an oscillating magnetic field. The sensing field may therefore oscillate with an amplitude at the source of between 0.1 mT and 2.0 mT; preferably between about 0.2 mT and about 1.2 mT.

In use, the sensing field generates a magnetic moment in the ferromagnetic material when the sensing probe is close to the marker, and the marker generates a detectable responding magnetic signal.

Under a sensing field of the kind described, it is desirable for the marker to be readily detectable. It is desirable for the marker to have a relatively strong net magnetic moment and produce a relatively high magnetic flux density (B) within the context of the sensing field. It is desirable that the magnetic flux is suitably isotropic (in practice a magnetic anisotropy ratio of less than 7, preferably less than 5, may suffice), so that the marker can be detected from reasonably far distances, and consistently from any direction. Under sensing fields, the magnetic signal generated by a marker is dominated by the at least one ferromagnetic element, as explained in more detail below. Fields of the magnitude described in the previous paragraph may typically allow the marker of the present disclosure to be detected at a range of up to about 50 mm, about 60 mm, about 70 mm or about 80 mm from the probe.

FIG. 2(*a*) is a hysteresis curve 1 showing magnetisation, M, as a function of applied magnetic field, H, for a typical ferromagnetic material. Ferromagnetic materials typically have a high initial magnetic susceptibility, as indicated by the dashed line 3, developing a strong magnetisation, M, when subject to a small applied magnetic field, H. FIG. 2(*b*) is a similar hysteresis curve 101 showing magnetic flux density, B, as a function of magnetic field, H, for atypical ferromagnetic material. Ferromagnetic materials typically reach magnetic saturation (at saturation induction $B_S$) 105 under relatively low applied magnetic fields (H). The magnetic moment of the ferromagnetic material 7, is in the same direction as the applied magnetic field 9, as shown in FIG. 2(*c*).

The magnetic moment, $m_{ferromagnet}$ of the one or more ferromagnetic elements in a sensing field is defined as $m_{ferromagnet}=\chi_{app,ferromagnet}H\cdot V_{ferromagnet}$. The magnetic flux density (B) or magnetic field produced by the total ferromagnetic material in the marker is given approximately by:

$$B_{ferromagnet} = \frac{\mu_0 \chi_{app,ferromagnet} H \cdot V_{ferromagnet}}{2\pi y^3}$$

where $\chi_{app,ferromagnet}$ is apparent susceptibility of the one or more ferromagnetic elements, which is dependent upon the size and shape of the or each ferromagnetic element, in particular the aspect ratio, $V_{ferromagnet}$ is the total volume of ferromagnetic material, $\mu_0$ is the magnetic permeability in a classical vacuum, and y is the distance from the marker. The magnetic signal produced by the one or more ferromagnetic elements is proportional to the magnetic flux density produced by the one or more ferromagnetic elements and will therefore be dependent upon the total volume of magnetic material (V ferromagnet), the strength of the applied field (H), and the apparent susceptibility of the magnetic material ($\chi_{app,ferromagnet}$). The apparent susceptibility of the magnetic material is much larger for a long, thin ferromagnetic element, and the strength of the magnetic signal produced by the at least one ferromagnetic element reduces with distance, y, away from the element (in inverse proportion to the distance cubed).

Figure 3A:
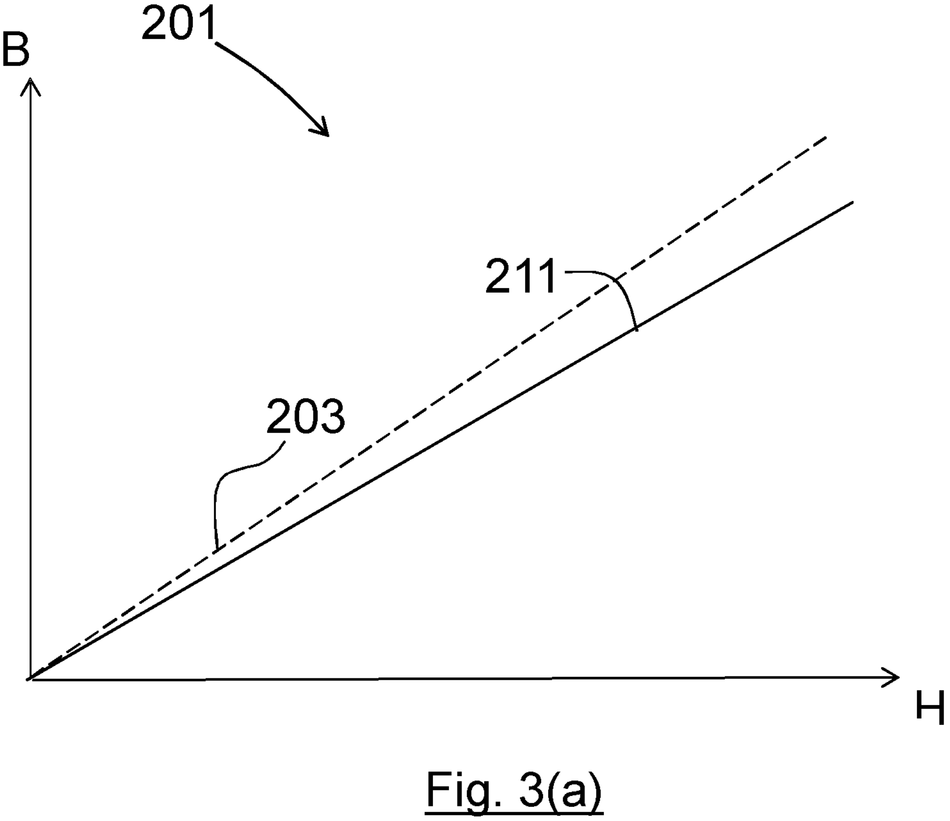
FIG. 3(*a*) is a graph showing magnetic flux, B, as a function of magnetic field, H, for a typical diamagnetic material (wherein the diamagnetic magnetisation shown is negative)
Figure 3B:
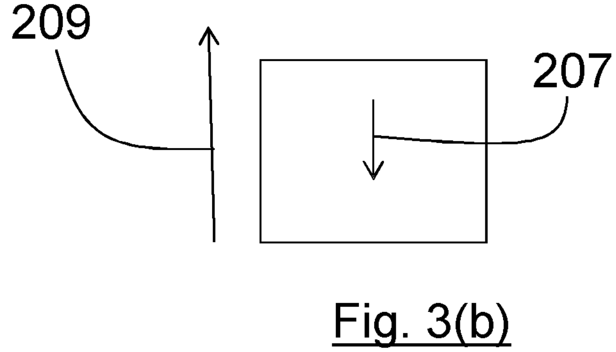

FIG. 3(*a*) is a graph 201 showing magnetic flux, B, as a function of magnetic field, H, for a typical diamagnetic material. As shown in FIG. 3(*a*), diamagnetic materials typically have low initial magnetic susceptibilities and show linear increases in magnetisation 211 up to relatively high magnetic fields, without reaching saturation. As a diamagnetic material, the magnetic flux B is less than that of free space, as indicated by dashed line 203 which is shown for reference, because the induced magnetisation opposes the magnetic field H. As shown in FIG. 3(*b*), when diamagnetic materials are subjected to an applied field, a magnetisation, or magnetic moment 207 is induced that opposes the direction of the applied field 209. As described herein, the at least one diamagnetic element of the present disclosure may have an initial (negative) susceptibility with a magnitude of less than $1\times10^{-3}$, typically less than about $3\times10^{-4}$, when subjected to a magnetic field of less than 0.01 mT. The magnetic moment, $m_{diamagnet}$ of the at least one diamagnetic element in a sensing field is defined as $m_{diamagnet}=\chi_{app,diamagnet}H\cdot V_{diamagnet}$. The magnetic flux density (B) generated by the diamagnetic element is given by:

$$B_{diamagnet} = \frac{\mu_0 \chi_{app,diamagnet} H \cdot V_{diamagnet}}{2\pi y^3}$$

wherein the $\chi_{app}$, diamagnet is the apparent susceptibility of the at least one diamagnetic element, which is dependent upon the size and shape of the at least one diamagnetic element, in particular the aspect ratio, $V_{diamagnet}$ is the total volume of diamagnetic material and y is the distance from the element. The at least one diamagnetic element of the present disclosure has a significantly smaller apparent susceptibility than the one or more ferromagnetic elements.

In a sensing field, the magnetic moment of the one or more ferromagnetic elements is high in relation to an opposing magnetic moment of the at least one diamagnetic element. The magnetic moment of the one or more ferromagnetic elements may be at least 1,000 to 1 million times greater in magnitude than the opposing magnetic moment of the at least one diamagnetic element Magnetic fields commonly used in MRI machines are several orders of magnitude stronger than the sensing fields described above, with the most common clinical MRI machines being 1.5 T or 3 T at the time of writing. In some embodiments of the present disclosure, therefore, the MRI magnetic field may typically be between 1 and 5 T, although in some embodiments it may be as high as 7 T or more.

As described above, the one or more ferromagnetic elements may reach saturation of induction at magnetic field strengths well below typical MRI magnetic field strengths. The one or more ferromagnetic elements of the present disclosure may have a saturation induction $B_S$ of 1.5 T or less and may therefore be saturated when subjected to an MRI magnetic field. In this case, using a dipole approximation, the magnetic moment, $m_{ferromagnet}$, of the one or more ferromagnetic elements when subject to the relatively strong MRI magnetic field is:

$$m_{ferromagnet} = M_s V_{ferromagnet} = \frac{B_s}{\mu_0} \cdot V_{ferromagnet},$$

where $\mu_0$ is the permeability of free space, $M_S$ is the magnetisation of the one or more ferromagnetic elements at saturation, and $V_{ferromagnet}$ is the total volume of ferromagnetic material. Advantageously therefore, in accordance with the present disclosure, the magnetic moment of the one or more ferromagnetic elements in an MRI field is limited by saturation of induction at the $B_S$ of the ferromagnetic elements. The magnetic moment of the one or more ferromagnetic elements may further be minimised by minimising the volume of ferromagnetic material used, in accordance with the disclosure of United Kingdom patent application no. 2115827.4. By way of example, the total magnetic moment of the one or more ferromagnetic elements may be of the order of about $2\times10^{-6}$ A·m$^2$ under an MRI field of 1.5 T.

When subject to an MRI magnetic field, the induced magnetic moment of the at least one diamagnetic element may also be significant, given the cap on the magnetisation of the one or more ferromagnetic elements owing to their saturation and the considerably greater volume of diamagnetic material used in the at least one diamagnetic element. The magnetic moment per unit volume of the at least one diamagnetic element will typically still be much weaker than that of the one or more ferromagnetic elements, but a significant volume of diamagnetic material relative to the volume of the ferromagnetic material may produce a magnetic moment that significantly negates the magnetic moment of the ferromagnetic material. When subject to a typical MRI field, the magnetic moment, $m_{diamagnet}$, from the at least one diamagnetic element is:

$$m_{diamagnet} = \frac{B_{MRI}}{\mu_0} \cdot \chi_{app,diamagnet} \cdot V_{diamagnet},$$

where $\chi_{app,diamagnet}$ is the apparent susceptibility of the at least one diamagnetic element.

By way of example, the total magnetic moment of the at least one diamagnetic element under an MRI field of 1.5 T may be of the order of about $-1\times10^{-6}$ A·m$^2$, where the negative sign indicates that the magnetic moment is in the opposite direction to the MRI field.

As the magnetic moment from the at least one diamagnetic element opposes the magnetic moment of the one or more ferromagnetic elements, the magnetic moment from the at least one diamagnetic element reduces the net magnetic moment of the marker as a whole when subject to an MRI field. The marker may suitably therefore have a net magnetic moment of less than about $1\times10^{-6}$ Am$^2$ when subjected to an MRI magnetic field. In particular, the marker may have a net magnetic moment of less than about $1\times10^{-6}$ Am$^2$ when subjected to a magnetic field of between 0.5 T and 7 T; preferably between about 1 T and 5 T; more preferably between about 1.5 T and 3 T.

Figure 4:
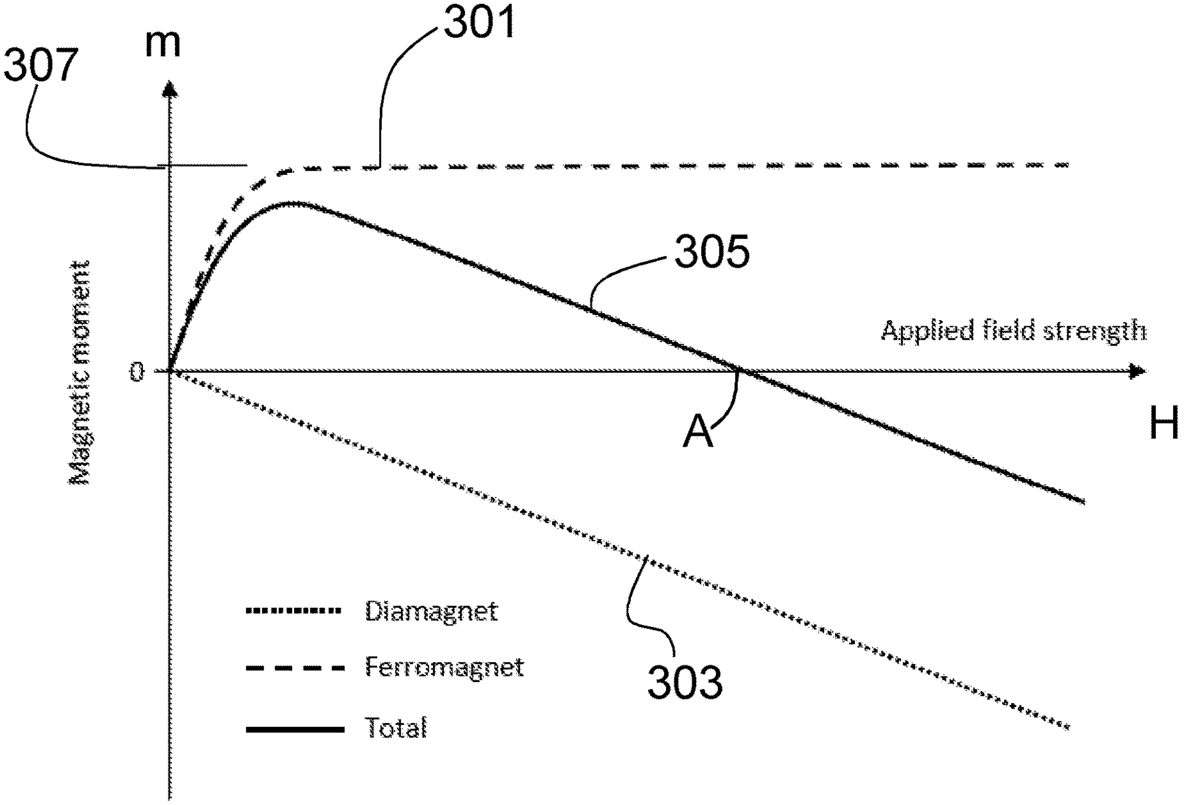
FIG. 4 shows schematically the variation in magnetic moment with applied magnetic field for a marker comprising at least one ferromagnetic element and at least one diamagnetic element according to an embodiment of the present disclosure.

FIG. 4 shows schematically the variation in magnetic moment with applied magnetic field H for a marker comprising one or more ferromagnetic elements and at least one diamagnetic element according to an embodiment of the present disclosure. Magnetic moment as a function of applied field is shown for the one or more ferromagnetic elements 301, the at least one diamagnetic element 303, and the total magnetic moment of the marker 305. At intermediate magnetic field strengths, below the strength of a typical MRI field, but above the strength of a sensing field, the one or more ferromagnetic elements have reached saturation 307 and the magnetic moment of the one or more ferromagnetic elements, $m_{ferromagnet}$, is relatively high. Meanwhile, the at least one diamagnetic element has an opposing magnetic moment that under a sensing field is very substantially smaller than the magnetic moment of the one or more ferromagnetic elements, but that increases linearly with applied field. At such intermediate fields, the magnetic moment of the one or more ferromagnetic elements still dominates the total magnetic moment, $m_{marker}$, 305, but at greater field strengths of the kind used in MRI scanners, the opposing (smaller) magnetic moment of the at least one diamagnetic element may represent a substantial proportion of the magnetic moment of the one or more ferromagnetic elements; for example, at least 25%, preferably at least 50%.

In some embodiments, at a certain applied magnetic field strength, indicated by point A, the amplitude of the (negative) magnetic moment of the at least one diamagnetic element may be substantially equal to the (positive) magnetic moment of the one or more ferromagnetic elements, and therefore the total, or net magnetic moment of the marker may be zero or close to zero. At even higher applied magnetic fields, the amplitude of the magnetic moment of the at least one diamagnetic element may even be larger than the amplitude of the magnetic moment of the one or more ferromagnetic elements, and the total, or net magnetic moment of the marker may be negative.

Given the constraints on the marker of the present disclosure in terms of its size and shape and the magnetic properties of available materials, the need to co-locate the magnetic dipoles induced within the one or more ferromagnetic elements and at least one diamagnetic element such that they coincide to cancel each out, at least to some degree, and the strength of the MRI magnetic field, it will be understood that in practice the magnetic moments of the one or more ferromagnetic elements and the at least one diamagnetic element may not cancel each other out completely. However, the object of the present disclosure may be satisfied as long as the magnetic moments of the one or more ferromagnetic elements and the at least one diamagnetic element offset one another sufficiently to reduce the artefact caused by the marker under MRI to an acceptable size; preferably less than about 30 mm in its longest dimension, more preferably less than 25 mm, and even more preferably less than about 20 mm.

Thus, in an MRI magnetic field, the opposing magnetic moments generated by a smaller one of the one or more ferromagnetic elements or, respectively, the at least one diamagnetic element may have an amplitude of at least 25%, preferably at least 50%, of the amplitude of a larger one of the magnetic moment produced by the at least one diamagnetic element or, respectively, the one or more ferromagnetic elements. In some embodiments, a smaller magnetic moment generated by the at least one diamagnetic element in an MRI field may have an amplitude of at least 27% of the amplitude of the magnetic moment produced by the one or more ferromagnetic elements; preferably at least 50% of the amplitude of the magnetic moment produced by the one or more ferromagnetic elements.

When subjected to an MRI field, the one or more ferromagnetic elements produce an artefact on an MRI image where the element causes a local change in the magnetic field in an MRI machine. The artefact is predominantly caused by the component of the magnetic flux produced by the ferromagnetic element $B_y$ that is in the same direction as the main field produced by the MRI machine (referred to herein as the y-axis). The effect of $B_y$ is to shift the local Larmor frequency of protons in tissue near the marker, and if that shift is large enough, those protons will not appear in the correct slice reconstructed by the MRI machine. That is, points at which $|B_y|\geq B_{crit}$ do not appear in the expected slice, where $B_{crit}$ is the magnitude of the y-component of the magnetic flux density B at which a voxel is mapped to a different slice, and the value of which depends on MRI scanning parameters.

The amount of ferromagnetic material, the saturation induction $B_S$ and the size and shape of the one or more ferromagnetic elements affect the size of the artefact. At distances that are large compared to the size of the one or more ferromagnetic elements, the magnetic flux density produced by the one or more ferromagnetic elements can be approximated by the dipole model. Along the axis of magnetisation, under that model, the magnetic flux density produced by the ferromagnetic element is given by:

$$B_y = \frac{\mu_0 m_{ferromagnet}}{2\pi y^3}$$

where $m_{ferromagnet}$ is the magnetic dipole moment of the one or more ferromagnetic elements and y is the distance from the object to the point of interest. As explained above, the magnetic moment, $m_{ferromagnet}$ of the one or more ferromagnetic elements in an MRI field is given by:

$$m_{ferromagnet} = M_s V_{ferromagnet} = \frac{B_s}{\mu_0} \cdot V_{ferromagnet}.$$

Combining these two equations, $$B_{ferromagnet,MRI} = \frac{B_s V}{2\pi y^3}$$

where $B_{ferromagnet,MRI}$ is the field produced by the one or more ferromagnetic elements in an MRI field. From this equation, it can be seen that when the marker is placed in an MRI machine and therefore is subject to a strong field, the strength of the magnetic field from the one or more ferromagnetic elements is dependent on the total volume of ferromagnetic material, its saturation induction and the distance away from it.

If one considers the edge of an MRI artefact, then at that point:

$$B_{ferromagnet,MRI}=B_{crit}$$

and y describes the distance from the centre of the artefact to its edge. At that point, using the equation above, one obtains:

$$y^3=\frac{B_s V}{B_{crit}2\pi}$$

and so:

$$y=\left(\frac{B_s}{B_{crit}}\cdot\frac{V}{2\pi}\right)^{\frac{1}{3}}$$

where $B_{crit}$ is an MRI scanning parameter defining the critical field at which an artefact is produced. If one defines the "diameter" of an artefact along the y-axis (although it may not be circular) as a measure of its extent as $D_{artefact,y}=2y$, then it follows that $$D_{artefact,y}=2\left(\frac{B_s}{B_{crit}}\cdot\frac{V}{2\pi}\right)^{\frac{1}{3}}.$$

In accordance with the present disclosure, the size of the artefact generated by the marker may be reduced by the presence of the at least one diamagnetic element, because the net magnetic moment of the marker is at least reduced by the presence of the at least one diamagnetic element. For the marker as a whole, when subject to an MRI field, the size of the artefact generated can be calculated as follows. As:

$$m_{total}=m_{ferromagnet}-m_{diamagnet}=\frac{B_s}{\mu_0}-V_{ferromagnet}-\frac{B_{MRI}}{\mu_0}\cdot\chi\cdot V_{diamagnet}$$

the total diameter of the artefact generated by the marker is given by:

$$D_{total,artefact,y}=2\left(\frac{m_{total}}{B_{crit}}\cdot\frac{\mu_0}{2\pi}\right)^{\frac{1}{3}}=2\left(\frac{1}{2\pi B_{crit}}\cdot(B_S V_{ferromagnet}-B_{MRI}\cdot\chi\cdot V_{diamagnet})\right)^{\frac{1}{3}}.$$

From this equation, it can be seen that in order to reduce or minimise the diameter of the artefact generated by the marker, $B_{MRI}\cdot\chi\cdot V_{diamagnet}$ needs to be comparable to $B_S\cdot V_{ferromagnet}$. Considering typical example values, if $B_{MRI}=1.5$ T, $B_S=0.6$ T, and $\chi=5\times10^{-4}$ then the volume of the at least one diamagnetic material would need to be at least about 1000 times greater than the volume of the one or more ferromagnetic elements in order to minimise the diameter of the artefact. However, as discussed in more detail below, the volume of diamagnetic material required to balance the magnetic moment of the one or more ferromagnetic elements will be smaller under a stronger MRI field, e.g. 3 T. In some embodiments, a volume of diamagnetic material that is less than about 10,000 times, for example less than 5,000 times or less than 2,500 times, e.g. about 1,000 times, greater than the volume of the one or more ferromagnetic elements may be suitable.

Large artefacts produced during MRI imaging are problematic and can lead to mismapping of spatial information. It is therefore important to minimise the size of the artefact generated by the marker in MRI magnetic fields, whilst still enabling the marker to be sensed in sensing fields.

In order for the marker to be sensed in sensing fields, the magnetic moment of the one or more ferromagnetic elements should dominate the net magnetic moment when the marker is subject to a sensing field.

In order for the artefact produced by the marker to be relatively small in typical MRI magnetic fields, the magnetic moment of the at least one diamagnetic element should at least partially offset the magnetic moment of the one or more ferromagnetic elements, such that the net magnetic moment of the marker is as small as possible. Additionally, the size and shape of an artefact generated by the one or more ferromagnetic elements alone should at least approximate the size and shape of an artefact generated by the at least one diamagnetic element alone, so that when combined together in close proximity within the marker they overlap and thus offset one another at least to some degree as described herein.

The size of the artefact generated by the markers of the present disclosure when subject to an MRI field is dependent upon the volume and shape of the one or more ferromagnetic elements and the volume and shape of the at least one diamagnetic element. Using a large volume of ferromagnetic material may lead to undesirably large artefacts. Increasing the volume of diamagnetic material may lead to a smaller artefact.

However, if a volume of diamagnetic material were to be used that was much greater than was required to offset the volume of ferromagnetic material, then a "negative" artefact generated by the at least one diamagnetic element may dominate over the artefact generated by the one or more ferromagnetic elements, and this may lead to an undesirable increase in the marker artefact size. It may therefore be desirable to optimise the volume ratio between the one or more ferromagnetic elements and the at least one diamagnetic element to reduce the size of the marker artefact size for a given MRI field strength.

As the size of the artefact generated in MRI magnetic fields is also dependent upon the $B_S$ of the one or more ferromagnetic elements, a greater volume of ferromagnetic material may be used if a ferromagnetic material with a lower $B_S$ is used. In some embodiments, the ferromagnetic material may have a $B_S$ in the range 0.25 T to 1.5 T.

The volume of diamagnetic material required to offset the magnetisation of the one or more ferromagnetic elements in an MRI field may depend on the strength of the MRI field. In particular, a smaller volume of diamagnetic material may be required to offset the saturated magnetisation of the one or more ferromagnetic elements in a stronger field. MRI scanners are available with different MRI field strengths, which means that the opposing magnetic moments of a marker comprising one or more ferromagnetic elements and at least one diamagnetic element may be of substantially equal magnitude under an MRI field of one strength, but unequal in a different MRI field. Suitably, the respective volumes of ferromagnetic and diamagnetic material in the marker of the present disclosure may give rise to MRI artefacts of acceptable sizes across a range of MRI fields; for example 0.5-10 T, preferably 1-7 T, and more preferably 1.5-3 T.

In some embodiments, the respective volumes of ferromagnetic and diamagnetic material in the marker may be such as to generate magnetic moments of substantially equal amplitude under one MRI field, e.g. 1.5 T, thereby to minimise the artefact size, while still giving rise to an acceptably small artefact under a different MRI field, e.g. 3 T. Preferably, in order to minimise the volume of material used in the marker, the amount of diamagnetic material present may be such that the amplitude of the magnetic moment generated by the at least one diamagnetic element is substantially equal to the amplitude of the magnetic moment generated by the one or more ferromagnetic elements under a first MRI field, e.g. 3 T, while still producing an artefact of acceptable size under a second MRI field, e.g. 1.5 T, which is weaker than the first MRI field.

In some embodiments, the respective volumes of ferromagnetic and diamagnetic material in the marker may be such as to generate magnetic moments of different amplitudes at two or more different MRI fields, but the artefact size under each different MRI field is of acceptable size. As disclosed herein, the marker may comprise relative amounts of ferromagnetic and diamagnetic materials such that the magnetic moments generated by at least one of them under at least two different MRI fields are each separately within about 75% of corresponding magnetic moments generated by other; preferably within about 50%. Thus, in some embodiments, the magnetic moments generated by the diamagnetic material may have amplitudes under at least two different MRI fields that are each separately within a range of about 25% to about 175% of corresponding amplitudes of the opposing magnetic moments generated by the one or more ferromagnetic elements; preferably within the range of about 50% to about 150%. In this sense, the respective amounts of ferromagnetic and diamagnetic material in the marker may be optimised to target an acceptably small artefact under two or more different MRI fields; particularly in the range about 0.5-10 T, preferably 1-5 T, e.g. at 1.5 T and 3 T. The shape and dimensions of the or each ferromagnetic element and the at least one diamagnetic element may also influence the size and shape of the artefact and the ease with which the marker can be sensed.

As disclosed in United Kingdom patent application no. 2115827.4, for a given volume of ferromagnetic material, a ferromagnetic element that has a large aspect ratio may be more readily detectable in sensing fields. Increasing a magnetic element's aspect ratio (L/D, e.g. where L is the length of the element and D is its diameter or width in the case of an element having a non-circular section) may increase its sense performance in the direction of its longer axis. As the ratio L/D increases, so does the apparent permeability $\mu_{app}$ of the element, which in turn may increase the distance at which it may be sensed. This phenomenon is due to the demagnetisation effect.

Suitably, the or each of the one or more ferromagnetic elements may comprise at least one wire or strip. The wire may comprise a cylindrical wire with a generally circular cross-section. Alternatively, the wire may be a flat wire or a strip. The one or more ferromagnetic elements may comprise a plurality of wires and/or strips.

In some implementations, one or more ferromagnetic elements in the form of multiple wires or strips may be configured to define a tortuous path or paths, either individually or in combination, extending in several different directions and/or including twists, bends, or turns in order to optimise the isotropy of the magnetic response of the marker as described herein and in UK patent application no. 2115827.4.

The one or more ferromagnetic elements of the marker of the present disclosure may suitably have a length to diameter (or square root of its cross-sectional area) (L D) ratio of at least 50.

The one or more ferromagnetic elements may suitably have a total volume of less than $1\times10^{-10}$ m$^3$; preferably less than about $1\times10^{-11}$ m$^3$, as described above.

Unless explicitly stated otherwise, the term "length" as used herein in the context of an individual magnetic element means the length of the element as if the element were extended in a linear manner. For example, in the case of a helical ferromagnetic element, the length of the element is the length of a wire forming the helix. By contrast, the phrase "overall length" is used herein, unless stated otherwise, to mean the length of one or more magnetic elements in the configuration in which it or they are formed within the marker. In the latter context, "length" generally refers to the size of the one or more elements in the direction of the longest dimension of the marker. Meanwhile, "overall diameter" or "overall width" means the diameter or width, respectively, of one or an assembly of more than one magnetic elements in a direction transverse the longest dimension.

A ferromagnetic element with a high aspect ratio and a low volume seeks to balance a useful sensing response with an acceptably small MRI artefact: reducing the volume of the ferromagnetic material may reduce the MRI artefact created by the ferromagnetic element. Meanwhile, increasing the aspect ratio of the at least one ferromagnetic element for a given volume of ferromagnetic material may improve the sensing response of the marker.

In some embodiments, the aspect ratio of the or each ferromagnetic element may be at least 100, at least 200, at least 300, at least 400, at least 500, at least 1000, at least 2000 or at least 3000. This allows for the sensing response to be maintained while the volume of the ferromagnetic material, and hence the MRI artefact size, is reduced. In some embodiments, the one or more ferromagnetic elements may have a total volume of less than $1\times10^{-11}$ m$^3$.

Increasing a ferromagnetic element's material's aspect ratio may dramatically increase its sense performance in the direction of its longest dimension. As the aspect ratio increases, so does the apparent permeability $\mu_{app}$ of the marker, which in turn increases the distance at which it can be sensed as a result of the demagnetisation effect.

A straight ferromagnetic wire has a high aspect ratio and produces a strong magnetic flux density in the direction of its longitudinal axis. This may lead to a practical sensing performance in a sensing field in a direction parallel to this axis. However, such an element may be less easy to detect in a direction perpendicular to the longitudinal axis, i.e. it may have an anisotropic sensing response and there may be a wide variation in the magnetic response of the element depending on its orientation to the sensing field, which may make it difficult to calibrate the magnetic response detected by a probe to its proximity to the marker. Using one or more ferromagnetic elements that have a large aspect ratio may result in a good sensing performance using a relatively small volume of ferromagnetic material, which has the benefit of producing a small artefact in an MRI image.

The sensing response under a sensing field and the MRI artefact size of a ferromagnetic element may depend on different variables. It has been recognised that under a sensing field, such as that produced by a Sentimag™ probe, the sense performance may depend almost exclusively on aspect ratio and volume of ferromagnetic material, with a weaker dependence on the initial relative permeability, $\mu_{r,i}$ (the initial gradient of the B-$\mu_0$H curve). By contrast, the magnitude of magnetic field produced by a ferromagnetic element when subjected to an MRI field, and hence the MRI artefact size, may depend on the saturation induction $B_S$ and volume of ferromagnetic material. This means that it is possible to limit the size of the MRI artefact by using a very thin piece of low-saturation-induction ferromagnetic material which may still be sensed at a satisfactory distance.

It has been found that a coiled ferromagnetic wire may have a more isotropic response in a sensing field than a straight wire, whilst still having a low volume and a high aspect ratio. A coiled ferromagnetic wire may therefore lead to an acceptably small artefact in an MRI field, whilst being detectable in a sensing field from an improved range of directions with less variation in its magnetic response with orientation to the sensing field.

In some embodiments therefore, the one or more ferromagnetic elements may comprise a coiled ferromagnetic wire or strip, or multiple spaced apart rings, which may be mutually substantially coaxial. Optionally, the one or more ferromagnetic elements may further include one or more straight rods extending through the coil or rings. In some implementations, at least one ferromagnetic element may comprise a helical wire coil.

In some embodiments, the one or more ferromagnetic elements may comprise at least one single helix; optionally combined with one or more straight wires arranged substantially parallel to a longitudinal axis of the helix.

In some embodiments, two or more of the ferromagnetic elements may be configured as a multiple helix, e.g. a double helix, triple helix or quadruple helix.

For a ferromagnetic element having the form of a single helix in combination with one or more ferromagnetic element having the form of straight wires or strips aligned substantially parallel to a longitudinal axis of the helix, a transverse magnetic response of the marker may result predominantly from the helix, and a longitudinal response may result predominantly from the one or more straight wires or strips.

Where the marker comprises more than one ferromagnetic element, individual ferromagnetic elements may be arranged such that they do not contact one another to avoid destructive interaction between the elements. In some embodiments, the ferromagnetic elements may be held apart by one or more spacers or by being secured to the at least one diamagnetic element or to another component of the marker; for example a housing or other non-magnetic support. Thus, in a multiple helix arrangement, for example, each individual helical ferromagnetic element may be arranged within a helical gap defined by the turns of one or more other helical ferromagnetic elements.

It has been found that the shape and size of an MRI artefact produced by a coiled magnetic wire may depend on the coil pitch and/or coil diameter of the wire. A greater pitch may typically produce a longer, thinner artefact, while a shorter, wider coil may typically produce a thicker, shorter artefact.

Suitably, the wire may have a diameter of less than about 100 μm, 50 μm, 30 μm, 15 μm, or 10 μm; preferably the wire may have a diameter of about 15 μm.

A helical ferromagnetic element formed from a ferromagnetic wire may have a helix diameter (i.e. the diameter of the helix) of between about 0.8 mm to 3 mm; preferably 1.0 mm and 1.5 mm; more preferably between about 1.15 mm and 1.30 mm, for example 1.2 mm. It has been found that a larger coil diameter may generate a stronger transverse sensing response in a sensing field.

Suitably, a helical ferromagnetic element may have a pitch of between about 0.5 mm and 3 mm; preferably about 1.4-1.8 mm, for example about 1.6 mm. A greater pitch may improve the sensing response of the helix in its axial direction. It is thought that this may be because a greater length of the helical coils projects in the axial direction.

Suitably, the pitch of the helix may be approximately equal to the diameter of the helix. In some embodiments, the pitch of the helix may be between 1.0-1.5 times the diameter of the helix. This may serve to maximise the transverse response of the helix in sensing fields.

Decreasing the pitch of a helical ferromagnetic element and increasing the number of turns may increase the transverse sensing performance of the marker, but may decrease its axial sensing performance. These may also increase the total length of wire used, which may increase the MRI artefact size for a given gauge of wire. Meanwhile, increasing the pitch and decreasing the number of turns of a helical ferromagnetic element may decrease the transverse sensing performance of the marker, but may increase its axial sensing performance. It may also decrease the total volume of wire used for a given wire gauge, which may serve advantageously to decrease the MRI artefact size of the marker. It has been found that there may be an optimum pitch to produce an isotropic sensing performance for each type of multiple helix marker. For a triple helix, a pitch of about 1.6 mm for each individual helix may be optimum for about a 1.6 mm diameter marker using a metal wire with diameter about 15 μm.

In some embodiments, the one or more ferromagnetic elements may comprise at least one helical ferromagnetic element having a helix length (i.e. the end-to-end length of the helix) of between about 2 mm and 10 mm; preferably between about 4 mm and 8 mm, for example about 5 mm. It has been found that a longer helix may increase the aspect ratio of the marker and may result in an improved sensing response. Suitably, the helical ferromagnetic element may be formed from a wire having a total length of at least about 3 mm, 6 mm, 10 mm, 30 mm, 50 mm, or 100 mm.

As described above, the at least one diamagnetic element may be configured and arranged to minimise the net magnetic moment of the marker in an MRI magnetic field. The at least one diamagnetic element may produce a "negative" artefact in an MRI field. The artefact produced by the at least one diamagnetic element may be calculated to reduce the size of the artefact generated by the marker as a whole, preferably at two or more MRI field strengths, as described above. Suitably, the at least one diamagnetic element may be configured and arranged to create an "inverse" artefact in an MRI field that has a similar shape and size to the artefact created by the one or more ferromagnetic elements.

For the at least one diamagnetic element most effectively to cancel out the field from the one or more ferromagnetic elements and therefore reduce the size of the resulting MRI artefact, the ferromagnetic and diamagnetic elements should therefore (i) produce fields of similar strength (but in opposite directions) in an MRI field; and (ii) be co-located as closely as possible.

Objective (i) above may be achieved in accordance with the present disclosure by using respective volumes of ferromagnetic and diamagnetic materials as disclosed herein, such that the two induced field strengths in an MRI field are similar. As disclosed herein, the at least one diamagnetic element may typically comprise a significantly greater volume of material than the one or more ferromagnetic elements.

Using a significantly larger volume of diamagnetic material as compared with the total volume of ferromagnetic material means that the total magnetic moment of the marker and therefore the size of the artefact produced by the marker may be reduced.

The volume of the at least one diamagnetic element may be about 100 to 10,000 times greater than the total volume of the one or more ferromagnetic elements; preferably about 500 to 3,000 times greater than the total volume of the one or more ferromagnetic elements; e.g. about 900 times. The total volume of the ferromagnetic material forming the one or more ferromagnetic elements may be less than $5\times10^{-11}$ $m^3$, $3\times10^{-11}$ $m^3$, or $1\times10^{-1}$ $m^3$, for example $6\times10^{-12}$ $m^3$. Typically, the volume of the at least one diamagnetic element may be between about $1\times10^{-9}$ $m^3$ and $1.5\times10^{-7}$ $m^3$, for example $6\times10^{-9}$ $m^3$.

Objective (ii) may be achieved by distributing the one or more ferromagnetic elements and at least one diamagnetic element in space in similar ways. Generally, the field produced by a given volume of diamagnetic material may be weaker than that produced by the same volume of ferromagnetic material, so a greater volume of diamagnetic material is necessary. Because of this, and because it may not be possible to co-locate the two materials perfectly, the fields generated by the two materials may not typically cancel one another out perfectly in an MRI field. It may be most beneficial to match the dipole components of the two fields, while matching higher-order components (quadrupole, octupole, etc.) may yield diminishing returns. Suitable configurations and arrangements of the ferromagnetic and diamagnetic elements may be determined empirically by using a suitable computer mathematical modelling program to produce contour maps of the magnetic flux changes that would be produced individually in an MRI field by the one or more ferromagnetic elements and at least one diamagnetic element and iteratively adjusting the configuration and arrangement of the elements until the contour maps substantially match. The shape and size of an artefact produced by one or more pieces of ferromagnetic or diamagnetic material in an MRI field may be represented by a contour line for $B_{crit}$ which, as mentioned above, for a given MRI field is the magnitude of the y-component of the change in magnetic flux density B at which a voxel is mapped to a different slice owing to the presence of the one or more pieces in the field.

The one or more ferromagnetic elements and at least one diamagnetic element may suitably be juxtaposed one another within a common space which may be defined by the one or more ferromagnetic elements and/or the at least one diamagnetic element. The one or more ferromagnetic elements and at least one diamagnetic element may advantageously be co-located. The one or more ferromagnetic elements and the at least one diamagnetic element may be configured and arranged such that a centre, e.g. a box centre (i.e. the centre of a notional rectangular box that fits as closely as possibly around an object) or geometric centre, of a theoretical artefact generated by the one or more ferromagnetic elements coincides with a centre, e.g. a box centre or geometric centre, of a theoretical artefact generated by the at least one diamagnetic element. In some embodiments, a centre of mass of the one or more ferromagnetic elements may substantially coincide with a centre of mass of the at least one diamagnetic element.

In some implementations, at least one ferromagnetic element may extend along or around an outer surface of the at least one diamagnetic element. In some implementations, at least one ferromagnetic element may be wrapped around the at least one diamagnetic element.

Conveniently, the at least one diamagnetic element may form a core of the marker. The at least one diamagnetic element may comprise an elongate body having an outer surface. Suitably, the elongate body may be substantially cylindrical. The elongate body may form a support or mandrel for at least one of the one or more ferromagnetic elements. In some implementations, at least one of the one or more ferromagnetic wires may be wrapped around the elongate body of the diamagnetic element to form a single or multiple helix, as described above. Alternatively, the at least one diamagnetic element may be disposed juxtaposed a single or multiple helix formed by at least one of the one or more ferromagnetic wires; for example in the form of an elongate rod which extends substantially parallel to a longitudinal axis of the helix or circumjacent the helix in the form of a hollow cylinder.

It has been found that the size of the artefact generated by the marker may advantageously be minimised if the overall length of the one or more ferromagnetic elements is the same as or similar to the overall length of the at least one diamagnetic element, and/or if the overall diameter or width of the one or more ferromagnetic elements is the same or similar to the overall diameter or width of the at least one diamagnetic element.

Suitably, therefore, the one or more ferromagnetic elements may extend individually or collectively along at least 80% of the overall length of the at least one diamagnetic element. In some embodiments, the at least one diamagnetic element may have an overall length of between about 2 mm and 10 mm; preferably between about 6 mm and 8 mm. In some implementations, the overall length of the at least one diamagnetic element may be approximately the same as the overall length of the one or more ferromagnetic elements; for example the helix length where the one or more ferromagnetic elements form a helix. The overall length of the at least one diamagnetic element may be within 25%, for example within 10%, for example within 5% of the overall length of the one or more ferromagnetic elements. The overall length of the at least one diamagnetic element may be within about 2% of the overall length of the one or more ferromagnetic elements.

Suitably, the marker may be sized to fit within a particular needle gauge; for example between 12 G and 18 G; preferably between 16 G or 18 G. In some embodiments, therefore, the marker may have a diameter in the range of about 0.514 mm to about 1.803 mm; preferably between about 0.838 mm and about 1.194 mm. Once the total volumes required for the ferromagnetic and diamagnetic materials have been defined, the proportion of each material within the marker can be calculated. The diameter, length and spatial arrangement of the one or more ferromagnetic elements and at least one diamagnetic element may then be determined based on the available diameter within a particular needle gauge, taking into account the need in some embodiments to accommodate a housing or outer coating for the ferromagnetic and diamagnetic elements.

Generally, the at least one diamagnetic element may have an overall diameter or width of between about 0.03 and 3 mm. Taking into account the internal diameter of a particular needle gauge, as discussed in the previous paragraph, and leaving enough room for a housing or outer coating, in some embodiments, the at least one diamagnetic element may have an overall diameter or width of between about 0.45 mm and 1.8 mm; more preferably between about 0.80 mm and 1.4 mm, for example 1.2 mm. It has been found that in many cases, having the overall diameters of the one or more ferromagnetic elements and at least one diamagnetic element as similar to each other as possible may lead to the best artefact size reduction. In some embodiments, the overall diameter of the at least one diamagnetic element may therefore be approximately the same as the overall diameter of the one or more ferromagnetic elements; for example the helical diameter where the one or more ferromagnetic elements form a helix. The overall diameter of the at least one diamagnetic element may be within about 5% of the overall diameter of the one or more ferromagnetic elements. The overall diameter of the at least one diamagnetic element may be within about 2% of the overall diameter of the one or more ferromagnetic elements. However, where a very strong diamagnetic material is used or the wire diameter is very thin, only a small amount of diamagnetic material may be needed to balance the ferromagnetic magnetic moment. In such cases, the overall diameter of the at least one diamagnetic element may be smaller than the overall diameter of the one or more ferromagnetic elements. Preferably, the similarity of the aspect ratio of the diamagnetic material with the one or more ferromagnetic elements will be conserved when the diameter of the diamagnetic element is smaller.

The one or more ferromagnetic elements and the at least one diamagnetic element may therefore be configured and arranged as disclosed herein, such that the artefact produced by the marker in an MRI magnetic field is less than about 30 mm in maximum length, preferably less than about 20 mm in maximum length. The size of the MRI artefact may vary depending on the strength of the MRI field. The artefact produced by the marker in an MRI magnetic fields may be less than 20 mm in length in a field of less than 3 T. The artefact produced by the marker in an MRI magnetic fields may be less than 20 mm in length in a field of less than 5 T. The artefact produced by the marker in an MRI magnetic fields may be less than 20 mm in length in a field of less than 7 T.

For markers according to embodiments of the present disclosure, it may be advantageous as described above for the one or more ferromagnetic elements to have a low saturation induction ($B_S$), for example, less than 1.5 T. Further, the one or more ferromagnetic elements may have a high initial relative permeability; for example greater than 1,000 for magnetic fields of between 0.1 mT and 0.5 mT. In some embodiments, the one or more ferromagnetic elements may have an initial relative permeability of more than 10,000. In some embodiments, the one or more ferromagnetic elements may have an initial relative permeability of more than 50,000 or even 100,000.

The or each ferromagnetic element may suitably comprise a ferromagnetic metal. At least one ferromagnetic element may comprise an amorphous metal. At least one ferromagnetic element may comprise a ceramic ferrite. Suitable ferromagnetic materials include cobalt-based amorphous metals; for example as sold under the trade names Yshield MCE61™, Metglas 2705M™ and Metglas 2714A™ Suitable ferromagnetic materials also comprise manganese-zinc ceramic ferrites; for example as sold under the trade names Fair-Rites 31™ 76™ and 78™. Suitable ferromagnetic materials further include nickel-iron-based soft ferromagnetic alloys; for example as sold under the trade names Mu-metal, Permalloy 80, Permalloy C, Permalloy and Supermalloy. Other suitable ferromagnetic materials comprise nickel-zinc ceramic ferrites; for example as sold under the trade names Fair-Rites 15™ 20™ and 43™; preferably cobalt-based amorphous metals, such as Yshield™ and Metglas 2714A™. Ceramics, however, while having a low saturation induction, are less easy to form into wire or flat wire and therefore are less suitable for a marker according to the invention. In some embodiments, metallic ferromagnetic materials may be preferred in view of their ductility for drawing into wires having a high aspect ratio and pliability for forming into rings, helices and the like.

Advantageously, the at least one diamagnetic element may be strongly diamagnetic, i.e. having a strong negative susceptibility of magnitude more than about $1\times10^{-4}$. This compares to the susceptibility of water which is about $-0.91\times10^{-5}$. In some embodiments, the at least one diamagnetic element may have a bulk or apparent bulk susceptibility between about $-1\times10^{-4}$ and $-3\times10^{-4}$. In some embodiments, the at least one diamagnetic element may have a bulk or apparent bulk susceptibility of up to about $-7\times10^{-4}$. A diamagnetic element having high (negative) susceptibility may be advantageous because it means that less diamagnetic material may be needed to offset the (positive) magnetisation of the one or more ferromagnetic elements in an MRI field.

In accordance with the present disclosure, the at least one diamagnetic element comprises graphite having a substantially isotropic grain structure, advantageously a fine grain structure. Isostatically-pressed graphite, for example, may have a suitably small grain size, and a higher density and higher strength than graphite formed from extrusion or compression moulding. Further, isostatically pressed graphite may advantageously have more isotropic properties than non-isotropic graphite formed for example by extrusion or compression moulding. Isostatically-pressed graphite may also be inexpensive, readily machinable, have good biocompatibility characteristics, and be produceable in grades with <5 ppm of impurities. Suitably, therefore, the graphite may be of high purity, containing more than 99.9% carbon. The graphite may have a density of at least about 1.75 g/cm$^3$, e.g. about 1.85 g/cm$^3$, which corresponds to a low porosity (e.g. of less than 15%). In some embodiments, the graphite may have a density of up to about 1.95 g/cm$^3$, or more. It has been found that high purity, high density, isostatically-pressed graphite has an apparent bulk susceptibility in an implantable marker according to the present disclosure of about $-1.2\times10^{-4}$.

The present disclosure, therefore, comprehends the use of graphite having a substantially isotropic grain structure in an implantable marker comprising one or more ferromagnetic elements for reducing the net magnetic moment of the marker in an MRI field, thereby to minimise the size of an artefact created by the marker. According to this embodiment, the implantable marker of the present disclosure may comprise one or more ferromagnetic elements and at least one diamagnetic element which is formed from graphite of high purity and having a substantially isotropic grain structure, for example by isostatic pressing. As described herein, the one or more ferromagnetic elements are advantageously arranged in juxtaposition with the at least one diamagnetic element.

The purity of the graphite may suitably be increased further by heat treatment; for example, at a temperature of at least about 2,200° C. Heat treatment may be carried out simultaneously with or subsequent to pressing or extruding the graphite.

According to embodiments, the present disclosure provides a method of manufacturing a magnetic marker. The method may comprise forming one or more ferromagnetic elements and at least one diamagnetic element wherein the diamagnetic element comprises graphite having a substantially isotropic grain structure, and thereafter assembling the one or more ferromagnetic elements with the at least one diamagnetic element to form the marker. The one or more ferromagnetic elements and at least one diamagnetic element may comprise respective volumes of ferromagnetic and diamagnetic materials that are selected as disclosed herein, such that in a sensing field, the one or more ferromagnetic elements are substantially more strongly magnetised than the at least one diamagnetic element, for generating a responding magnetic field of sufficient magnitude to allow the marker to be detected in tissue using a handheld probe, while in an MRI field, the at least one diamagnetic element has a degree of magnetisation which is sufficiently strong to offset at least a substantial proportion of the magnetisation of the one or more ferromagnetic elements, thereby minimising the size of the artefact produced by the marker. The one or more ferromagnetic elements may be configured and arranged to maximise the strength and isotropy of a responding field generated in response to the sensing field. The at least one diamagnetic element may be configured and arranged such that it would produce an artefact in the MRI field which has a size and shape that matches the artefact size and shape of an artefact that would be produced by the one or more ferromagnetic elements, at least to a sufficient degree as to reduce to the maximum dimension of the artefact created by the marker to less than about 30 mm; preferably less than about 20 mm. The graphite may be high purity, high density graphite.

In embodiments of the present disclosure, the method may comprise configuring and arranging the one or more ferromagnetic elements and the at least one diamagnetic element to produce mutually opposing magnetic moments in the presence of an applied magnetic field. The strength of the magnetic moment produced by the at least one diamagnetic element in relation to the strength of the magnetic moment produced by the one or more ferromagnetic elements may be negligible in a sensing field, to allow the magnetic moment produced by the at least one ferromagnetic element to be detected with a probe, and may of the same order of magnitude as the strength of the magnetic moment produced by the one or more ferromagnetic elements in an MRI field, thereby to minimise the size of an artefact produced by the marker on an MRI image by offsetting or substantially balancing the magnetic moment of the at least one ferromagnetic element.

In some embodiments, the method further includes the step of performing an isostatic pressing process to provide the isostatically pressed graphite.

In some embodiments, the method further includes the step of heat treating the graphite at a temperature in excess of 2,200 degrees Celcius.

In some embodiments, the step of configuring and arranging the one or more ferromagnetic elements and the at least one diamagnetic element may comprise wrapping the one or more ferromagnetic elements around a core or mandrel formed of the at least one diamagnetic element. Thus, in one embodiment of the present disclosure there is provided a method for manufacturing a marker comprising a diamagnetic core which is received in a coil of one or more ferromagnetic wires or strips. The core may have an initial length of several times the length of a single marker. The one or more ferromagnetic wires or strips may be wound around the diamagnetic core. The ends of the wires or strips may conveniently be secured to the core, for example using an adhesive, at the start and end of winding. The resulting assembly may then be divided into two or more segments, each segment having a length which corresponds to a length of the marker. The segments may be divided from one another by cutting, e.g. by mechanical, pressure or thermal means; for example with a blade, a water jet or a laser. Alternatively, the diamagnetic core may be cut into separate segments before the coil winding.

Figure 5:
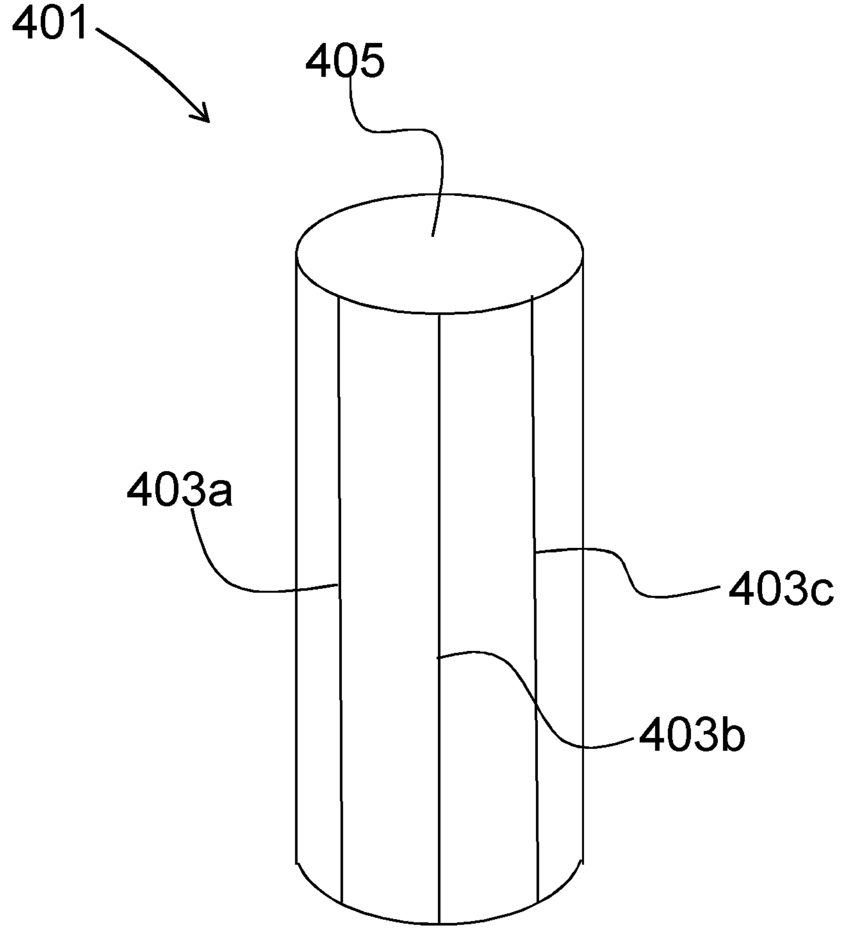
FIG. 5 is a schematic perspective view of an implantable marker comprising a cylindrical diamagnetic core and three spaced ferromagnetic wires which each extend substantially parallel to a longitudinal axis of the core, juxtaposed an outer surface thereof, according to a first embodiment of the present disclosure.

FIG. 5 is a schematic drawing of an implantable marker 401 according to an embodiment of the present disclosure. The marker 401 comprises three, generally linear ferromagnetic wires formed from an iron-cobalt based alloy 403*a*, 403*b*, 403*c* running along the outside of a diamagnetic core 405. It will be understood that in variants of this embodiment, fewer or more ferromagnetic wires may be used. The diamagnetic core 405 is a cylinder with a bulk susceptibility value of $\chi=-1.66\times10^{-4}$. The cylinder comprises isostatically pressed graphite and has a diameter of about 1 mm and a length of about 8 mm. The ferromagnetic wires 403*a*, 403*b*, 403*c* have an initial bulk susceptibility value of about 72,000. Each wire 403*a*, 403*b*, 403*c* has a diameter of about 16 μm, and a length of about 8 mm, and the wires 403*a*, 403*b*, 403*c* extend in a direction substantially parallel to a longitudinal axis of the core 405, such that the length of the wires substantially matches the length of the diamagnetic core 405.

In a sensing field of less than about 0.5 mT, the magnetic field generated by each of the wires 403*a*, 403*b*, 403*c* is proportional to the apparent susceptibility of the wire, $\chi_{app}$, wire, multiplied by the volume of the wire, $V_{wire}$, and the magnetic moment generated by the diamagnetic core 405 is proportional to the apparent susceptibility, $\chi_{app,core}$, of the core 405 multiplied by its volume, $V_{core}$. The quantity $\chi_{app,wire}\cdot 3\cdot V_{wire}$ for the combination of the wires 403*a*, 403*b*, 403*c* may be calculated to be about $4.6\times10^{-8}$ m$^3$, and the quantity $\chi_{app,core}V_{core}$ for the diamagnetic core 405 may be calculated to be about $-1.0\times10^{-12}$ m$^3$. The combined magnetic field generated by the ferromagnetic wires 403*a*, 403*b*, 403*c* in the sensing field is therefore about 45,000 times greater than the magnetic moment generated by the diamagnetic core 405, which is negligible in comparison.

When subjected to an MRI field of 1.5 T, each of the ferromagnetic wires 403*a*, 403*b*, 403*c* has reached saturation of induction. The combined magnetic moment of the three wires 403*a*, 403*b*, 403*c* is thus given by:

$$3m_{ferromagnet} = \frac{3B_s V_{wire}}{\mu_0}$$

where $B_S$ is the saturation induction of the wire, $\mu_0$ is the permeability of free space and $V_{wire}$ is the volume of one of the ferromagnetic wires. In this example, each wire has a $B_S$ value of 0.55 T, and $3m_{ferromagnet}=2.1\times10^{-6}$ Am$^2$. The diamagnetic core 405 does not saturate, and its magnetic moment is given by:

$$m_{diamagnet} = \frac{\chi_{app} V_{core} B_0}{\mu_0}$$

where $B_0$ is the MRI field, $\chi_{app}$ is the apparent susceptibility of the diamagnetic core 405, and $V_{core}$ is the volume of the diamagnetic core. For this marker 405, this gives $m_{diamagnet}$−=−1.2×10$^{-6}$ Am$^2$. Comparing the magnetic moments of the diamagnetic core 405 and the ferromagnetic wires 403*a*, 403*b*, 403*c* under a 1.5 T MRI field, the magnetic moment of the diamagnetic core 405 is about 57% of the magnetic moment of the ferromagnetic wires 403*a*, 403*b*, 403*c*.

Figures 6A, 6B:
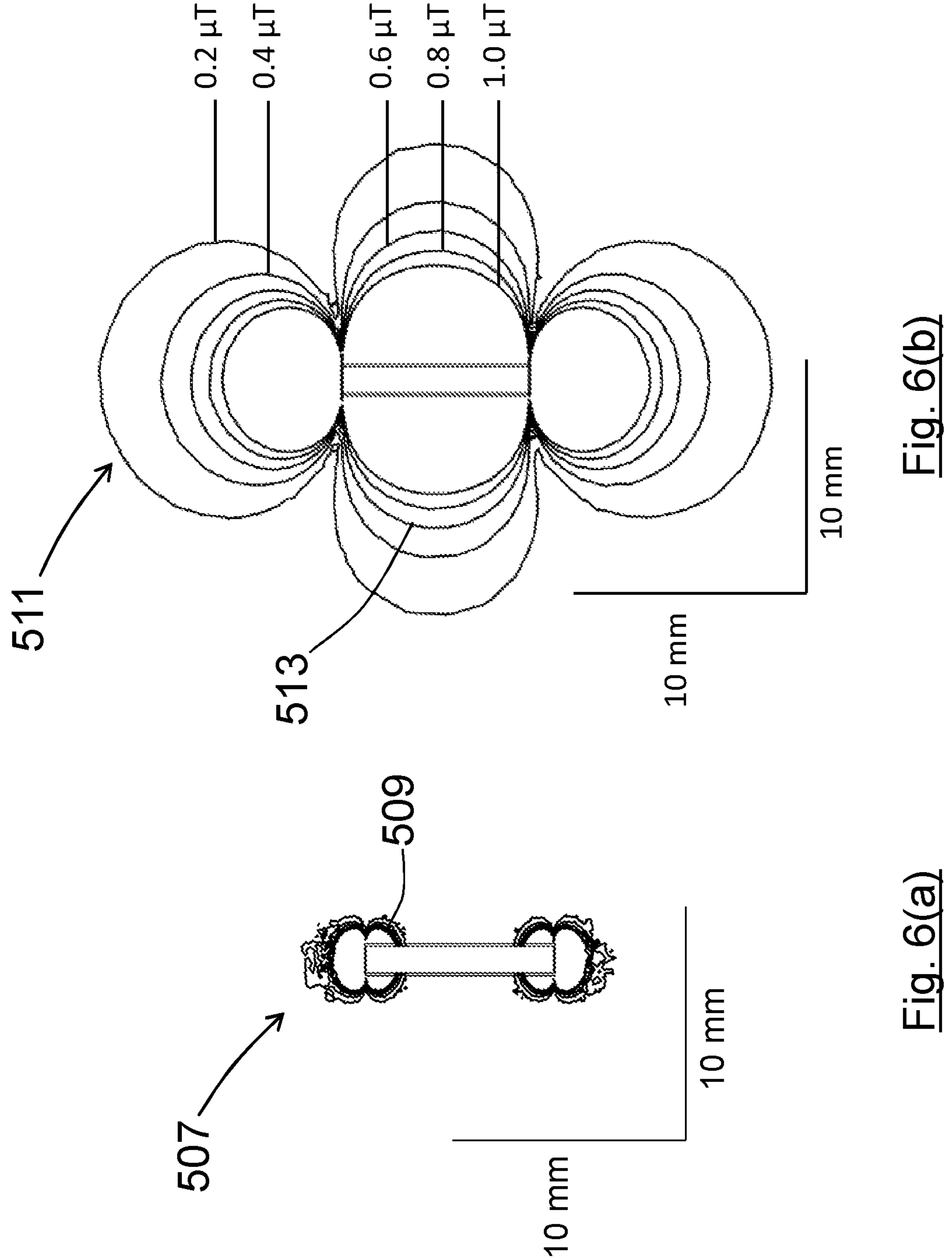
FIG. 6(*a*) is a contour map of magnetic flux density B in an x-z plane of an MRI scanner of the kind illustrated in FIG. 1(*a*) and/or FIG. 1(*b*), which shows how B deviates from an MRI field $B_0$ applied along the y-axis as a result of the presence in the field of the implantable marker of FIG. 5.

FIG. 6(*a*) is a contour map 507 showing the deviation $|B-B_0|_y$ in magnetic flux $B_y$ from an MRI field $B_0$ of 3 T across an x-z plane of an MRI scanner, which results from the presence of the marker 401 of FIG. 5 in the MRI field. The contour lines represent lines of constant flux density deviation in the vicinity of the marker 401. As discussed above, $B_{crit}$ is the magnitude of $|B-B_0|_y$ above which a voxel is mapped to an incorrect slice of an MRI image. A contour line at $B_{crit}$ thus represents an outline of an artefact which may be generated in the x-z plane for the marker 401 of FIG. 5 in the MRI field, wherein the axial length of the marker 401 is oriented along the y-axis. It has been found that a value of $B_{crit}$ of 0.6 μT, indicated by contour line 509, gives reasonably good agreement between theoretical predictions and experimental data, but those skilled in the art will appreciate that $B_{crit}$ will depend on the configuration of a particular MRI machine (e.g. slice thickness). FIG. 6(*a*) therefore shows other contours at different values of $|B-B_0|_y$ to show how the artefact size varies for different values of $B_{crit}$.

For comparison, FIG. 6(*b*) is a contour map 511 showing the deviation $|B-B_0|_y$ in magnetic flux density $B_y$ which would be generated in the same MRI field $B_0$ for the same configuration of ferromagnetic wires 403*a*, 403*b*, 403*c* in the absence of the diamagnetic core 405. Contour line 513 represents $B_{crit}$ 0.6 μT. The effect of the diamagnetic core on reducing the size of the artefact in the x-z plane in FIG. 6(*a*) is self-evident.

Figure 7:
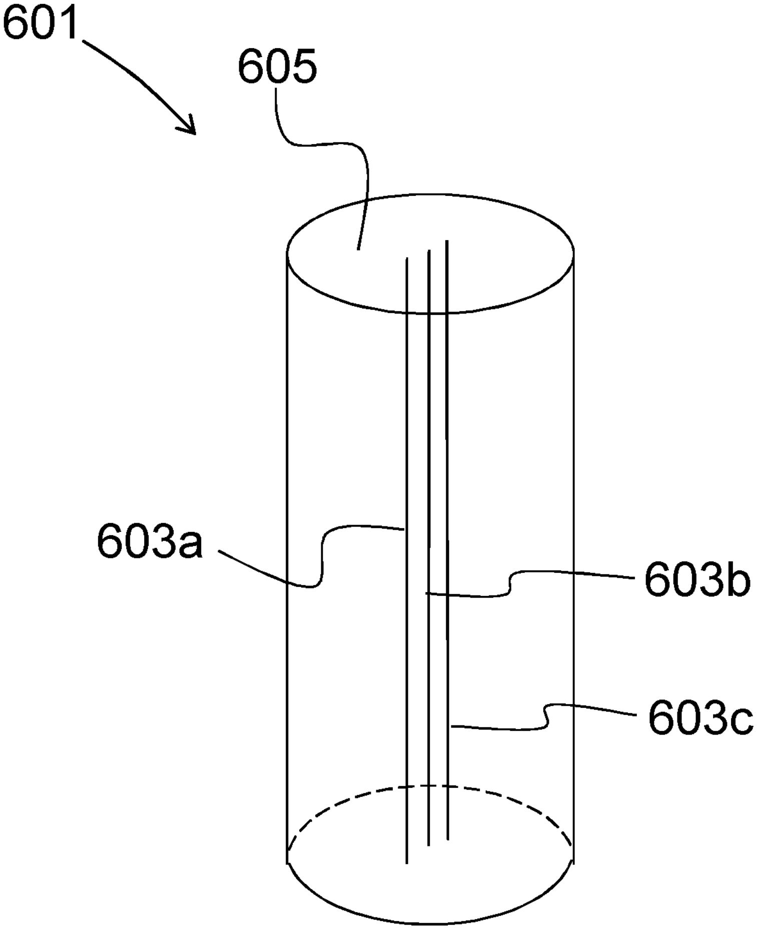
FIG. 7 is a schematic perspective view of an implantable marker comprising a cylindrical diamagnetic core and three spaced ferromagnetic wires which each extend through the diamagnetic core, substantially parallel to its longitudinal axis, according to a second embodiment of the present disclosure.

FIG. 7 is a schematic drawing of a different implantable marker 601 according to an embodiment of the present disclosure. Similar to the marker 401 of FIG. 5 described above, the marker 601 comprises three ferromagnetic wires 603*a*, 603*b*, 603*c*, although in variants fewer or more wires may be used. However, in this embodiment, the ferromagnetic wires 603*a*, 603*b*, 603*c* extend axially through a diamagnetic core 605. The diamagnetic core 605 is substantially the same size and shape, and has substantially the same properties as the diamagnetic core 405 of FIG. 5. Thus, the core 605 is a cylinder of isostatically pressed graphite with a bulk susceptibility value of $\chi$=−1.66×10$^{-4}$. The cylinder has a diameter of about 1 mm and a length of about 8 mm. The ferromagnetic wires 603*a*, 603*b*, 603*c* are substantially the same length and gauge as the wires 403*a*, 403*b*, 403*c* shown in FIG. 5. Thus, the ferromagnetic wires 603*a*, 603*b*, 603*c* have an initial bulk susceptibility value of about 72,000. Each wire 403*a*, 403*b*, 403*c* has a diameter of about 16 μm, and a length of about 8 mm, such that the length of the wires substantially matches the length of the diamagnetic core 405.

Figure 8:
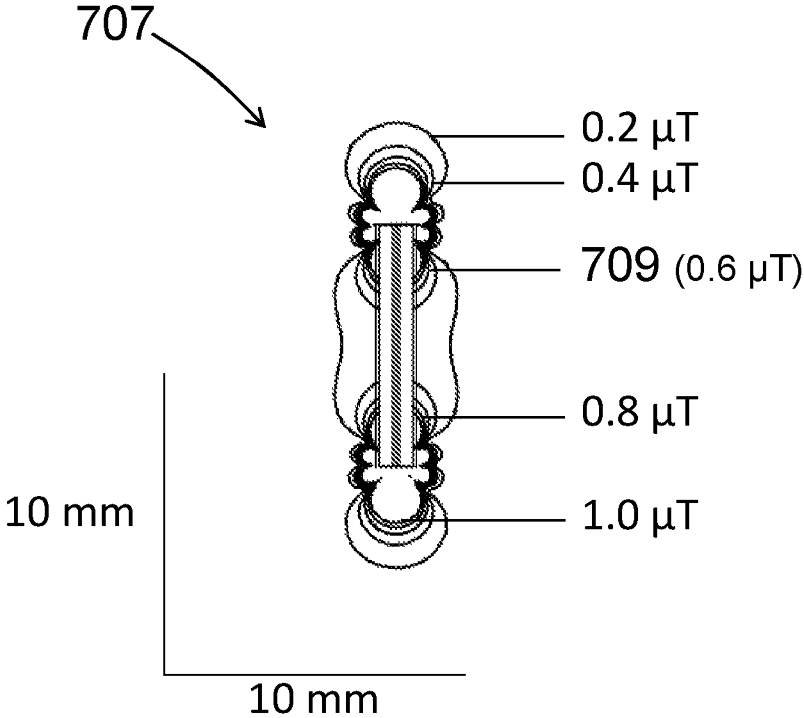
FIG. 8 is a contour map of magnetic flux density B in an x-z plane of an MRI scanner of the kind illustrated in FIG. 1(*a*) and/or FIG. 1(*b*), which shows how B deviates from an MRI field $B_0$ as a result of the presence in the field of the implantable marker of FIG. 7.

FIG. 8 is a contour map 707 which is similar to FIG. 6(*a*), showing the deviation $|B-B_0|_y$ in magnetic flux B, from an MRI field $B_n$ of 3 T across an x-z plane of an MRI scanner which results from the presence of the marker 601 of FIG. 7 in the MRI field, wherein the axial length of the marker 601 is oriented with the y-axis. As in FIGS. 6(*a*) and 6(*b*), a contour line 709 at 0.6 μT, which may correspond to $B_{crit}$, thus represents an outline of an artefact which may be generated in the x-z plane for the marker 601 in the MRI field. $B_y$ comparing the artefacts of FIG. 6(*a*) and FIG. 8, it can be seen that the overall size and shape of the artefact in the x-z plane does not change significantly depending on whether the ferromagnetic wires 403*a*, 403*b*, 403*c*; 603*a*, 603*b*, 603*c* are disposed outside or inside of the diamagnetic core 405; 605.

Figure 9:
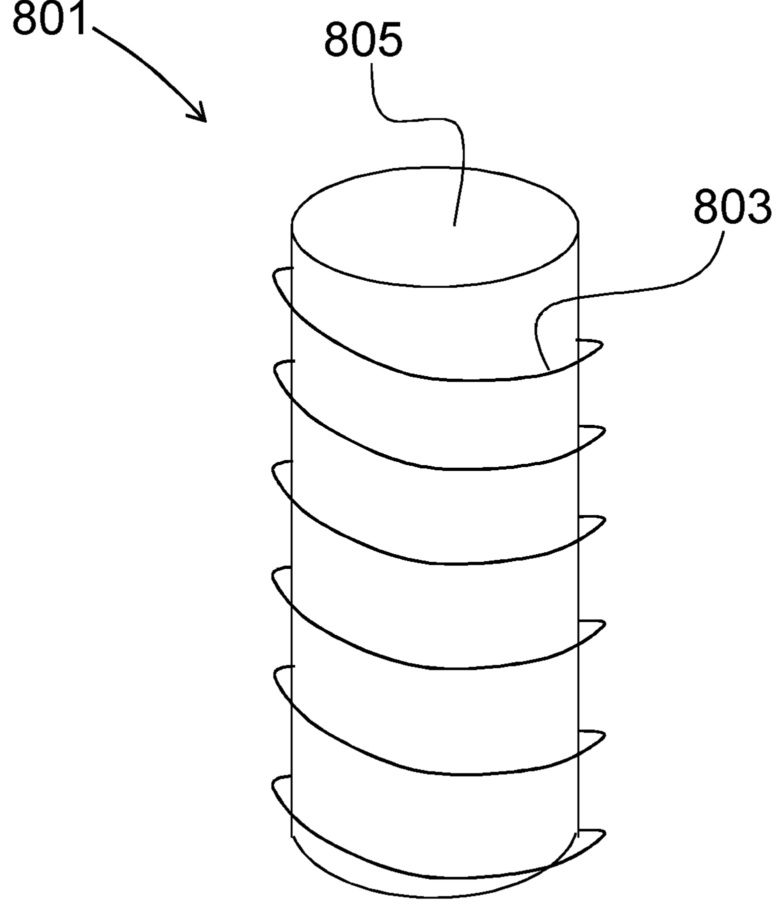
FIG. 9 is a schematic perspective view of an implantable marker comprising a cylindrical diamagnetic core and a ferromagnetic wire helix which extends around an outer surface of the diamagnetic core, according to a third embodiment of the present disclosure.

FIG. 9 is a schematic drawing of another implantable marker 801 according to an embodiment of the present disclosure. The marker 801 comprises a substantially cylindrical diamagnetic core 805 of isostatically pressed graphite or another suitable diamagnetic material as disclosed herein, having a diameter of about 1.15 mm and a length of about 8 mm. The diamagnetic core 805 has a susceptibility of about −1.2×10$^{-4}$. The marker 801 further comprises a ferromagnetic element, which consists of a single helical coil of wire 803 of an iron-cobalt based alloy. It will be appreciated that other ferromagnetic materials may be used, as disclosed herein. The wire 803 has a diameter of about 15 μm, and the helix has a length of about 8 mm (i.e. about the same length as the core 805). The helix has a pitch of about 1.2 mm. In variants of this embodiment, a plurality of ferromagnetic wires may be wrapped around the diamagnetic core 805 in the form of a multiple helix, e.g. a double helix or triple helix. This may allow the same amount of wire to be used but with a longer pitch to increase the sensitivity of the marker as disclosed herein.

Figures 10A, 10B:
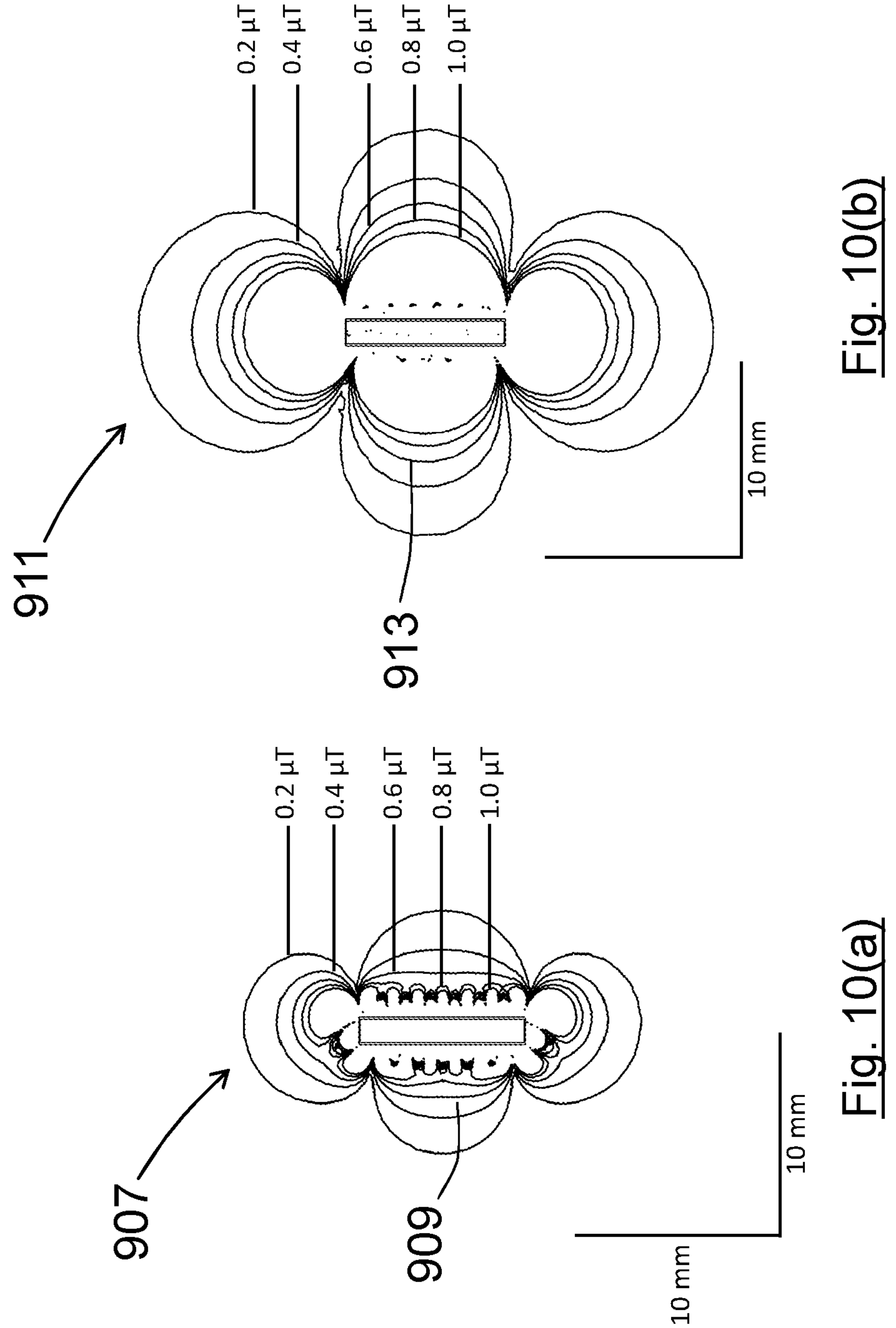
FIG. 10(*a*) is a contour map of magnetic flux density B in an x-z plane of an MRI scanner of the kind illustrated in FIG. 1(*a*) and/or FIG. 1(*b*), which shows how B deviates from an MRI field $B_0$ as a result of the presence in the field of the implantable marker of FIG. 9.

FIG. 10(*a*) is a contour map 907 which is similar to those of FIGS. 6(*a*) and 8, showing the deviation $|B-B_0|_y$ in magnetic flux density $B_y$ from the MRI field $B_0$ of 3 T across an x-z plane of an MRI scanner, which results from the presence of the marker 801 of FIG. 9 in the MRI field, wherein the axial length of the marker 801 is oriented with they-axis. As in FIGS. 6(*a*), 6(*b*) and 8, a contour line 909 at 0.6 μT, which may correspond to $B_{crit}$, thus represents an outline of an artefact which may be generated in the x-z plane for the marker 801 in the MRI field. For comparison, FIG. 10(*b*) is a contour map 911 showing the deviation $|B-B_0|_y$ in magnetic flux density $B_y$ which would be generated in the same MRI field $B_0$ for the same ferromagnetic helix 803, in the absence of the diamagnetic core 805. Contour line 913 represents $B_{crit}$ 0.6 μT. The effect of the diamagnetic core on reducing the size of the artefact in the x-z plane in FIG. 10(*a*) is self-evident.

Figure 11:
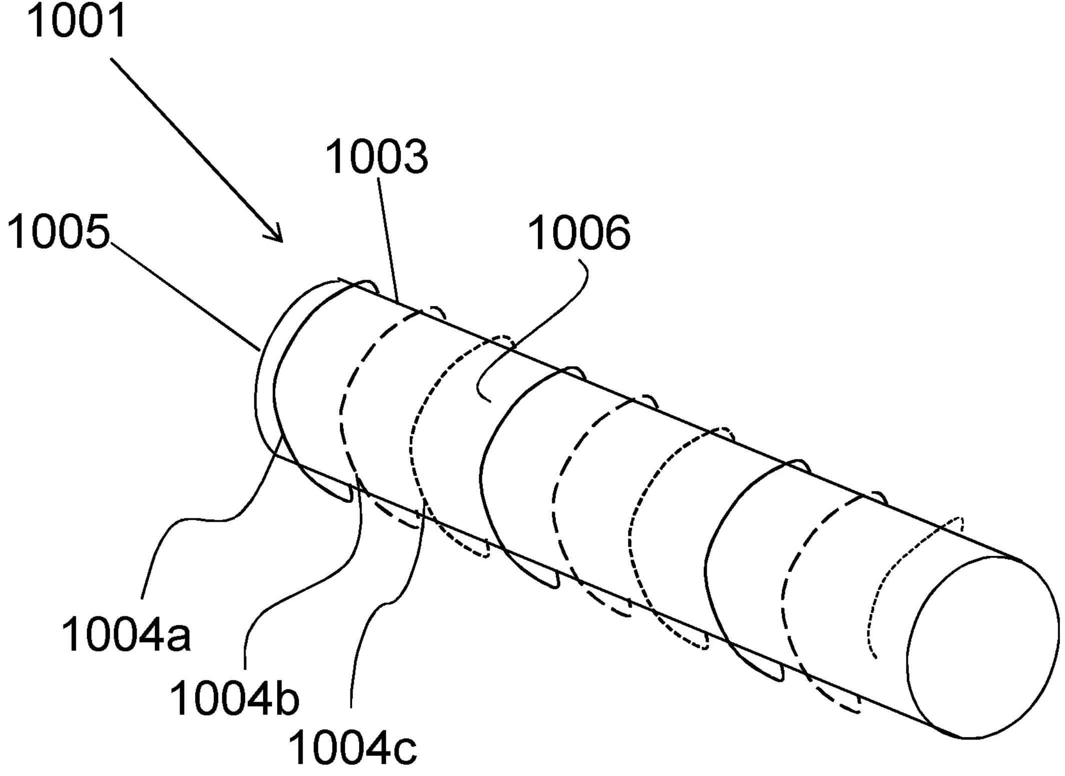
FIG. 11 is a schematic perspective view of an implantable marker comprising a cylindrical diamagnetic core and a triple helix formed from ferromagnetic wires which extends around an outer surface of the diamagnetic core, according to a fourth embodiment of the present disclosure.

FIG. 11 is a schematic drawing of yet another implantable marker 1001 according to an embodiment of the present disclosure. The marker 1001 has a substantially cylindrical diamagnetic core 905 of isostatically pressed graphite, which has a diameter of about 1.15 mm and a length of about 8 mm. The diamagnetic core 1005 has a susceptibility of about −1.2×10$^{-4}$. The diamagnetic core 1005 has a cylindrical outer surface 1006 which supports three ferromagnetic elements 1004*a*, 1004*b*, 1004*c*. Each ferromagnetic element 1004*a*, 1004*b*, 1004*c* comprises a coil of wire of a ferromagnetic iron-cobalt-based material, the wire having a diameter of about 15 μm. As shown in FIG. 11, the coils are arranged to form a triple helix 1003 with the respective wires 1004*a*, 1004*b*, 1004*c* not contacting one another. Suitably, the wires may be bonded or otherwise retained in position on the outer surface 1005. Each coil of the triple helix has a pitch of about 1.80 mm. Each coil in the triple helix 1003 comprises about 4.4 turns of wire, such that the total number of turns in the triple helix 1003 is about 14.2. The total length of ferromagnetic wire used in the triple helix is about 52 mm (in another example embodiment, it may be less than 52 mm, for example less than 40 mm).

Figures 12A, 12B:
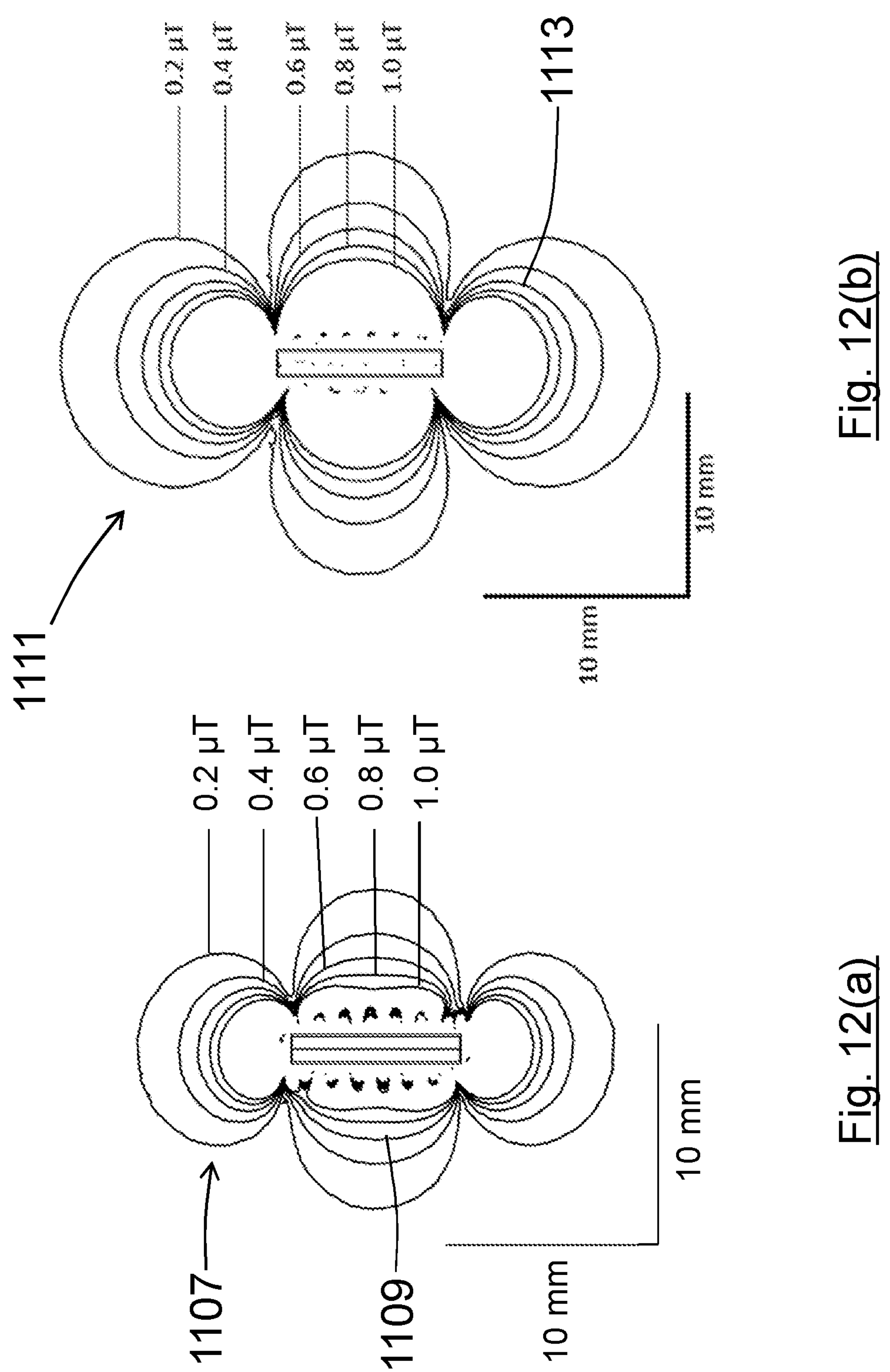
FIG. 12(*a*) is a contour map of magnetic flux density B in an x-z plane of an MRI scanner of the kind illustrated in FIG. 1(*a*) and/or FIG. 1(*b*), which shows how B deviates from an MRI field $B_0$ as a result of the presence in the field of the implantable marker of FIG. 10 in the field.

In an MRI field of about 1.5 T, the total magnetic moment of the three ferromagnetic wires 1004*a*, 1004*b*, 1004*c* is calculated to be about $2.1\times10^{-6}$A·m$^2$. Meanwhile, the magnetic moment of the diamagnetic core 1005 is about $-1.2\times10^{-6}$A·m$^2$. The net magnetic moment of the marker 1001 of the present embodiment in the 1.5 T MRI field is therefore about $8.7\times10^{-7}$ A·m$^2$. FIG. 12(*a*) is a contour map 1107 showing the deviation $|B-B_0|_y$ in magnetic flux density $B_y$ from an MRI field $B_0$ of 3 T across an x-z plane of an MRI scanner, which results from the presence of the marker 1001 of FIG. 11 in the MRI field. The contour lines represent lines of constant flux deviation in the vicinity of the marker 1001. As discussed above, $B_{crit}$ is the magnitude of $|B-B_0|_y$ above which a voxel is mapped to an incorrect slice of an MRI image. A contour line at $B_{crit}$ thus represents an outline of an artefact which may be generated in the x-z plane for the marker 1001 of FIG. 11 in the MRI field, wherein the axial length of the marker 1001 is oriented along the y-axis. It has been found that a value of $B_{crit}$ of 0.6 T, indicated by contour line 1109, gives reasonably good agreement between theoretical predictions and experimental data, but those skilled in the art will appreciate that $B_{crit}$ will depend on the configuration of a particular MRI machine (e.g. slice thickness). FIG. 12(*a*) therefore shows other contours at different values of $|B-B_0|_y$ to show how the artefact size varies for different values of $B_{crit}$.

For comparison, FIG. 12(*b*) is a contour map 1111 showing the deviation $|B-B_0|_y$ in magnetic flux density $B_y$ which would be generated in the same MRI field $B_0$ for the same configuration of ferromagnetic wires 1004*a*, 1004*b*, 1004*c* in the absence of the diamagnetic core 1005. Contour line 1113 represents $B_{crit}$=0.6 μT. The effect of the diamagnetic core on reducing the size of the artefact in the x-z plane in FIG. 12(*a*) is self-evident.

Using a triple helix 1003 may allow the same amount of wire to be used as a single helix within a given axial length, but with a longer pitch to increase the axial sensitivity of the marker, as the coils of the helix have a larger component of their direction along the axial length of the marker. A pitch of about 1.80 mm has been found to provide sufficient transverse sense performance whilst having a good axial sense performance resulting from the longer pitch. In this embodiment, the axial sense distance of the marker is about 34 mm, and the transverse sense distance is about 34 mm.

Figure 13:
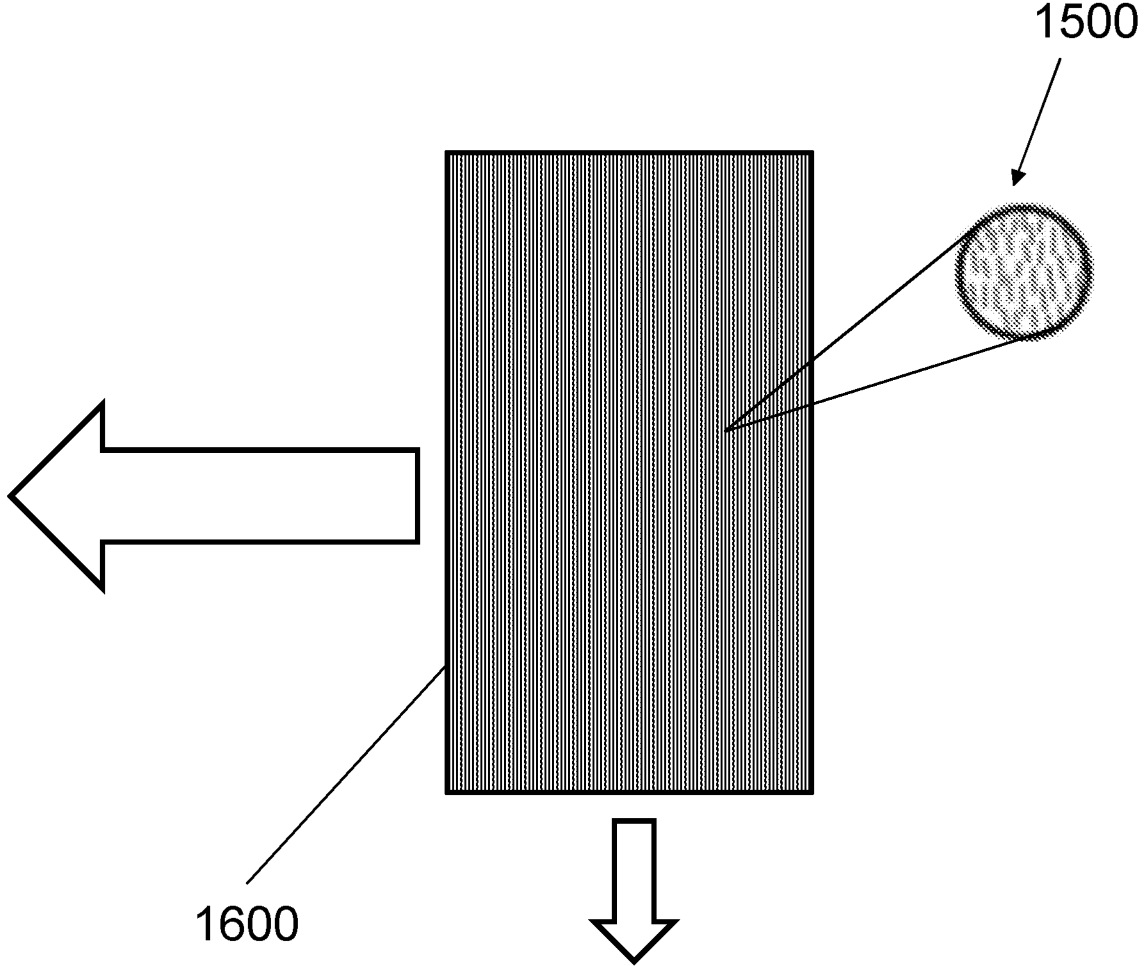
FIG. 13 is a diagram of graphite having an anisotropic grain structure.

FIG. 13 of the accompanying drawings shows a typical grain structure 1500 of a graphite rod 1600 having an anisotropic grain structure (for example being formed from extruded graphite), wherein the grains are aligned longitudinally. The magnetic susceptibility of the graphite is higher in an against-grain direction, and lower in a with-grain (i.e. longitudinal) direction.

Figure 14:
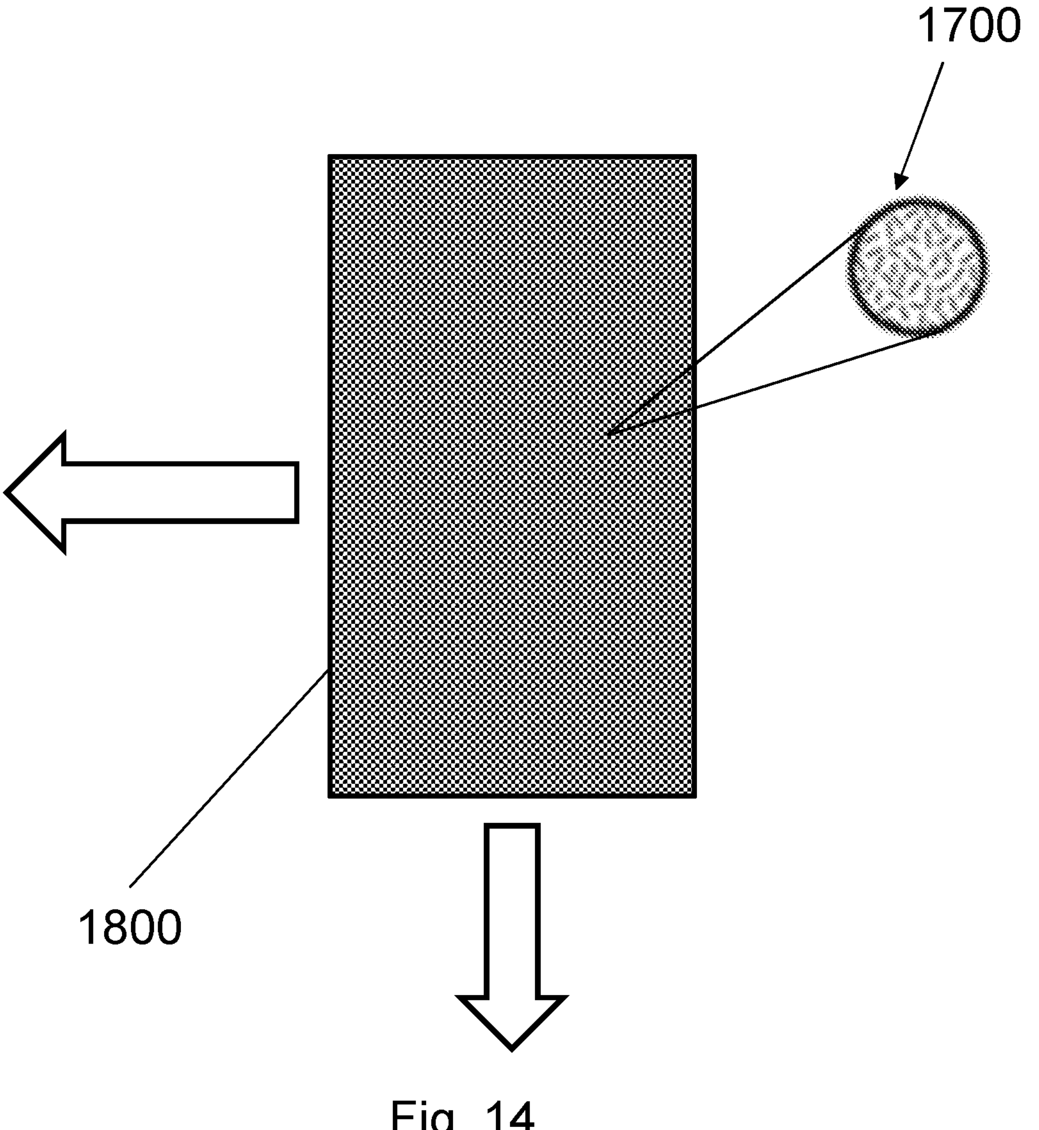
FIG. 14 is a diagram of graphite having an isotropic grain structure.

FIG. 14 of the drawings shows a typical grain structure 1700 of a graphite rod 1800 having an isotropic grain structure (for example being formed from isostatically pressed graphite), wherein the grains are oriented randomly (not aligned). The magnetic susceptibility of the graphite may be moderate to high in all directions.

Figure 15:
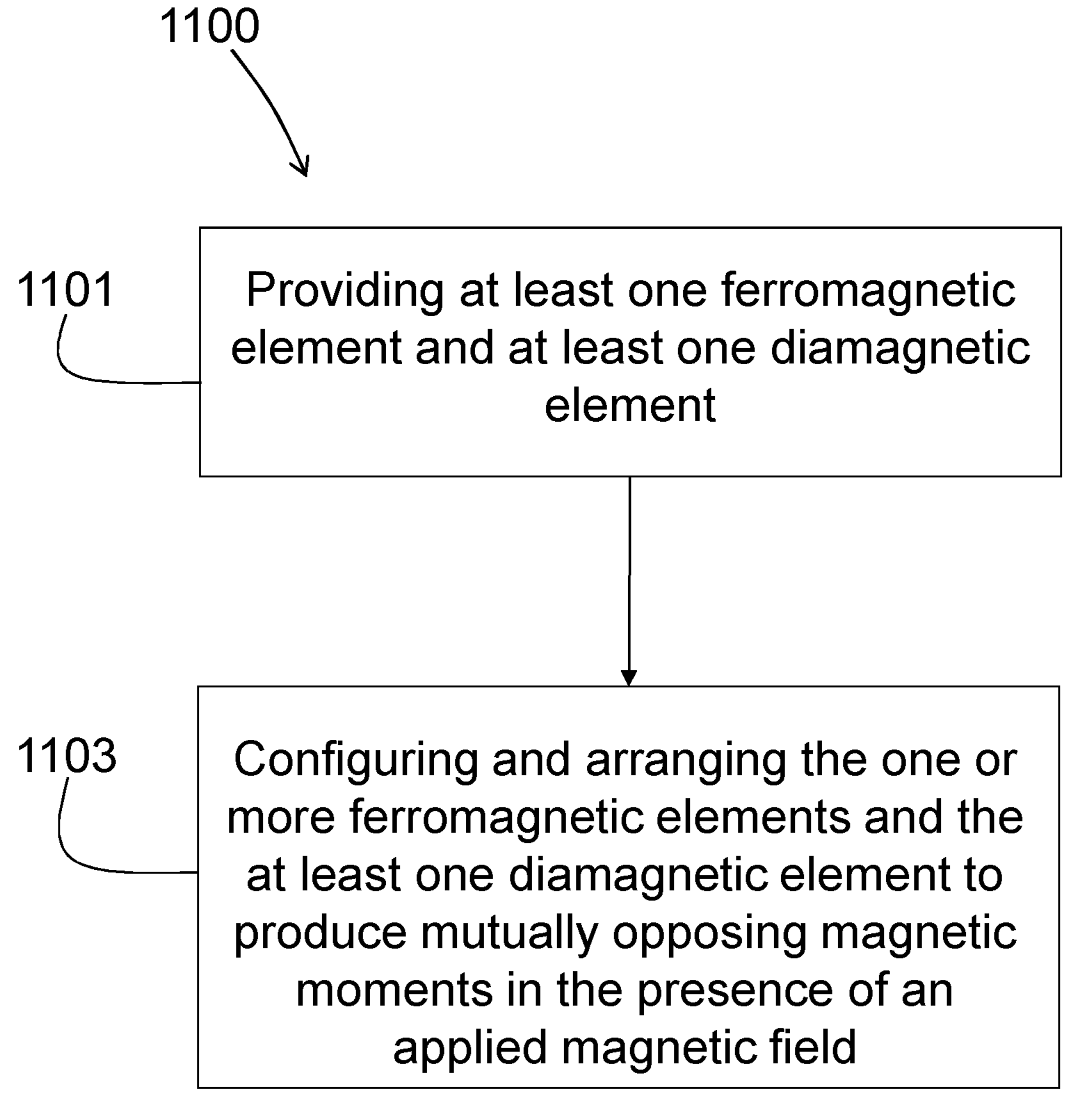
FIG. 15 is a flowchart showing a method of manufacturing an implantable marker, according to a fifth embodiment of the present disclosure.

FIG. 15 is a flowchart showing a method 1100 of manufacturing a marker, according to an embodiment of the present disclosure. In a first step 1101, the method comprises providing at least one ferromagnetic element and at least one diamagnetic element wherein the diamagnetic element comprises graphite having a substantially isotropic grain structure. In a second step 1103, the method comprises configuring and arranging the one or more ferromagnetic elements and the at least one diamagnetic element juxtaposed one another such that they are co-located to produce mutually opposing magnetic moments in the presence of an applied magnetic field. The strength of the magnetic moment produced by the at least one diamagnetic element in relation to the strength of the magnetic moment produced by the at least one ferromagnetic element is relatively very low in a sensing field of less than about 0.5 mT, thereby to allow the magnetic moment produced by the at least one ferromagnetic element to be detected with a probe, and is relatively high in an MRI magnetic field of 1.5 T or more, thereby to minimise the size of an artefact produced by the marker on an MRI image by offsetting the magnetic moment of the at least one ferromagnetic element.

The ferromagnetic material configured into the required shape may then be encapsulated in a cylindrical housing. The cylindrical housing is preferably injectable in order to allow for placement of the marker. Suitably, therefore, the housing may have a maximum diameter such that it is deployable through a narrow gauge needle e.g. 18 G to 12 G, as disclosed above. The marker may be packaged within other materials, or a coating may be applied to the marker, to ensure that the marker is biocompatible and robust. The marker may be encased in a tube, for example made from Nitinol, titanium, stainless steel or other biocompatible alloys, the material preferably being non-magnetic and having a relatively low conductivity. A low conductivity may comprise a conductivity of below $10^6$ Siemens. Suitable coating materials include a polymer coating, such as Invar®, FEP, Parylene®, PTFE, ETFE, PE, PET, PVC or silicone or an epoxy based encapsulant.

It will be appreciated by those skilled in the art that features of the above-described embodiments may be combined in other embodiments that fall within the scope of the present disclosure.

Whilst in the foregoing description, integers or elements are mentioned which have known obvious or foreseeable equivalents, then such equivalents are herein incorporated as if individually set forth. Reference should be made to the claims for determining the true scope of the present disclosure, which should be construed as to encompass any such equivalents. It will also be appreciated by the reader that integers or features of the disclosure that are described as advantageous, convenient or the like are optional, and do not limit the scope of the independent claims. Moreover, it is to be understood that such optional integers or features, whilst of possible benefit in some embodiments of the disclosure, may not be desirable and may therefore be absent in other embodiments.

The invention claimed is:

1. An implantable marker for use in surgical guidance comprising one or more ferromagnetic elements formed of at least one ferromagnetic material; and at least one diamagnetic element formed of at least one diamagnetic material; wherein the at least one diamagnetic material comprises graphite having a substantially isotropic grain structure and the one or more ferromagnetic elements are juxtaposed the at least one diamagnetic element, wherein the graphite is isostatically pressed graphite.

2. The implantable marker as claimed in claim 1, wherein the graphite has a bulk susceptibility of more than $-0.16\times10^{-4}$.

3. The implantable marker as claimed in claim 1, wherein the graphite has an apparent bulk susceptibility in the marker of more than $-0.9\times10^{-4}$.

4. The implantable marker as claimed in claim 1, wherein the isostatically pressed graphite has an apparent bulk susceptibility in the marker of at least about $-1.2\times10^{-4}$.

5. The implantable marker as claimed in claim 4, wherein the isostatically pressed graphite contains fewer than 300 ppm of impurities.

6. The implantable marker as claimed in claim 4, wherein the isostatically pressed graphite contains more than 99.9% carbon.

7. The implantable marker as claimed in claim 1, wherein the isostatically pressed graphite has a density of at least about 1.75 $g/cm^3$ and optionally has a density of about 1.85 $g/cm^3$.

8. The implantable marker as claimed in claim 1, wherein the graphite is heat treated graphite.

9. The implantable marker as claimed in claim 1, wherein the one or more ferromagnetic elements comprise one or more wires or strips of ferromagnetic material having a length to diameter (or length to square root of cross-sectional area) ratio of at least 50.

10. The implantable marker of claim 1, wherein the ferromagnetic material comprises a ferromagnetic metal, amorphous metal or ceramic ferrite.

11. An implantable marker for use in surgical guidance comprising:

one or more ferromagnetic elements formed of at least one ferromagnetic material; and at least one diamagnetic element formed of at least one diamagnetic material;

wherein the at least one diamagnetic material comprises graphite having a substantially isotropic grain structure and the one or more ferromagnetic elements are juxtaposed the at least one diamagnetic element, and wherein the at least one diamagnetic element has a total volume that is about 100-10,000 times greater than a volume of the one or more ferromagnetic elements.

12. A method of manufacturing an implantable magnetic marker for use in surgery, the method comprising steps of:

forming one or more ferromagnetic elements from at least one ferromagnetic material;

forming at least one diamagnetic element, wherein the at least one diamagnetic element comprises isostatically pressed graphite having a substantially isotropic grain structure; and thereafter assembling the one or more ferromagnetic elements and the at least one diamagnetic element such that the one or more ferromagnetic elements are juxtaposed the at least one diamagnetic element, wherein the one or more ferromagnetic elements and the at least one diamagnetic element are configured and arranged to produce mutually opposing magnetic moments in a presence of an applied magnetic field.

13. The method of manufacturing the implantable magnetic marker as claimed in claim 12, wherein the method includes step of performing an isostatic pressing process to provide the isostatically pressed graphite having the substantially isotropic grain structure.

14. The method of manufacturing the implantable magnetic marker as claimed in claim 12, further comprising step of heat treating the graphite at a temperature in excess of about 2,200 degrees Celsius.

15. A detection system for locating an implantable marker, the system comprising:

the implantable marker for use in surgical guidance comprising one or more ferromagnetic elements formed of at least one ferromagnetic material and at least one diamagnetic element formed of at least one diamagnetic material; wherein the at least one diamagnetic material comprises graphite having a substantially isotropic grain structure and the one or more ferromagnetic elements are juxtaposed the at least one diamagnetic element, wherein the implantable marker is configured to be detected by a susceptibility probe;

at least one drive coil arranged to excite the implantable marker with an alternating magnetic field and at least one sense coil arranged to detect a signal received from the excited implantable marker;

a magnetic field generator arranged to drive an alternating magnetic field through the at least one drive coil; and at least one detector arranged to receive the signal from the sense coil and detect one or more harmonics of the drive frequency in the received signal, wherein the susceptibility probe comprises the at least one detector; and wherein the graphite is isostatically pressed graphite.

16. The detection system of claim 15, wherein the at least one diamagnetic element has a total volume that is about 100-10,000 times greater than a volume of the one or more ferromagnetic elements.

17. The detection system of claim 15, wherein the strength of the sensing field gives rise to a field strength that ranges from about 40 μT and about 400 μT within about 5 mm of the susceptibility probe.

18. The detection system of claim 17, wherein the strength of the sensing field gives rise to a field strength that ranges from about 40 μT to about 400 μT within about 5 mm of the susceptibility probe.

19. The implantable marker of claim 15, wherein the alternating magnetic field is a sensing field, wherein the sensing field has a strength that ranges from about 0.1 mT to about 2.0 mT.

20. The implantable marker of claim 19, wherein the strength of the sensing field gives rise to a field strength that ranges from about 40 μT to about 400 μT within about 5 mm of the susceptibility probe.

* * * * *